United States Patent
Hasegawa

(10) Patent No.: US 9,597,269 B2
(45) Date of Patent: *Mar. 21, 2017

(54) SURFACE-TREATED POWDERS AND COSMETIC COMPOSITIONS IN WHICH SUCH POWDERS ARE MIXED

(71) Applicant: MIYOSHI KASEI, INC., Saitama-shi, Saitama (JP)

(72) Inventor: Yukio Hasegawa, Saitama (JP)

(73) Assignee: MIYOSHI KASEI, INC., Saitama (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/424,091

(22) PCT Filed: Dec. 26, 2012

(86) PCT No.: PCT/JP2012/008345
§ 371 (c)(1),
(2) Date: Feb. 26, 2015

(87) PCT Pub. No.: WO2014/102862
PCT Pub. Date: Jul. 3, 2014

(65) Prior Publication Data
US 2015/0224036 A1  Aug. 13, 2015

(51) Int. Cl.
| | | |
|---|---|---|
| *A61K 8/89* | (2006.01) |
| *A61K 8/25* | (2006.01) |
| *A61Q 1/02* | (2006.01) |
| *A61Q 5/02* | (2006.01) |
| *A61K 8/29* | (2006.01) |
| *A61Q 1/10* | (2006.01) |
| *A61Q 1/12* | (2006.01) |
| *A61Q 5/12* | (2006.01) |
| *A61Q 17/04* | (2006.01) |
| *A61Q 19/00* | (2006.01) |
| *A61K 8/19* | (2006.01) |
| *C09C 3/12* | (2006.01) |
| *A61K 8/02* | (2006.01) |
| *A61Q 1/06* | (2006.01) |
| *A61Q 3/02* | (2006.01) |
| *A61Q 1/04* | (2006.01) |
| *A61K 8/891* | (2006.01) |

(52) U.S. Cl.
CPC ............... *A61K 8/25* (2013.01); *A61K 8/022* (2013.01); *A61K 8/0241* (2013.01); *A61K 8/19* (2013.01); *A61K 8/29* (2013.01); *A61K 8/89* (2013.01); *A61K 8/891* (2013.01); *A61Q 1/02* (2013.01); *A61Q 1/04* (2013.01); *A61Q 1/06* (2013.01); *A61Q 1/10* (2013.01); *A61Q 1/12* (2013.01); *A61Q 3/02* (2013.01); *A61Q 5/02* (2013.01); *A61Q 5/12* (2013.01); *A61Q 17/04* (2013.01); *A61Q 19/00* (2013.01); *A61Q 19/002* (2013.01); *A61Q 19/007* (2013.01); *C09C 3/12* (2013.01); *A61K 2800/61* (2013.01); *A61K 2800/614* (2013.01)

(58) Field of Classification Search
None
See application file for complete search history.

(56) References Cited

U.S. PATENT DOCUMENTS

| 5,744,126 A | 4/1998 | Horino et al. |
| 2012/0171136 A1* | 7/2012 | Sonoyama ............... A61Q 1/02 424/63 |

FOREIGN PATENT DOCUMENTS

| EP | 1 579 841 A1 | 9/2005 |
| JP | S45-002915 B1 | 1/1970 |
| JP | S45-018999 B1 | 6/1970 |
| JP | S63-152308 A | 6/1988 |
| JP | H08-6035 B2 | 1/1996 |
| JP | 2582275 B2 | 2/1997 |
| JP | H09-48716 A | 2/1997 |
| JP | H09-255528 A | 9/1997 |
| JP | H10-251123 A | 9/1998 |
| JP | 3079395 B2 | 8/2000 |
| JP | 2002-128637 A | 5/2002 |
| JP | 2004-315468 A | 11/2004 |

(Continued)

OTHER PUBLICATIONS

Feb. 5, 2013 International Search Report issued in International Application No. PCT/JP2012/008345.
Feb. 5, 2013 Written Opinion issued in International Application No. PCT/JP2012/008345.
Nov. 13, 2015 Amendments to Reasons for Rejections issued in Japanese Patent Application No. 2014-553882.
Nov. 13, 2015 Reasons for Rejections issued in Japanese Patent Application No. 2014-553882.
Feb. 5, 2013 International Search Report issued in International Patent Application No. PCT/JP2012/008346.
Feb. 5, 2013 Written Opinion issued in International Patent Application No. PCT/JP2012/008346.
Sep. 16, 2015 Reasons for Rejections issued in Japanese Patent Application No. 2014-553883.
Amendments to Sep. 16, 2015 Reasons for Rejection issued in Japanese Patent Application No. 2014-553883.
Argument to Sep. 16, 2015 Reasons for Rejection issued in Japanese Patent Application No. 2014-553883.

(Continued)

*Primary Examiner* — H. Sarah Park
(74) *Attorney, Agent, or Firm* — Oliff PLC

(57) ABSTRACT

The invention is directed to the cosmetic powder surface-treated with a silicone gel, wherein the surface treatment with the silicone gel affords excellent water repellency, the exhibits smooth and light touch, and affords moist usability peculiar to the silicone gel and excellent adhesion to skin for the cosmetic powder. The powder is an inorganic powder, an organic powder or a composite powder thereof. The silicone gel is obtained by hydrolysis and condensation reacting an organopolysiloxane containing at least a diorganopolysiloxane having reactive opposite ends shown in the following formula (1) and a silane coupling agent having the following formula (2) with at least two hydrolyzable groups in one molecule or a reactive polysiloxane of the following formula (3) as a crosslinking agent. (1) $R^1R^2{}_2SiO-(R^2{}_2SiO)_L-SiR^1R^2{}_2$; (2) $R^3R^4nSiX_{(3-n)}$; and (3) $R^5{}_3SiO-(R^5{}_2SiO)n-SiR^5{}_3$.

29 Claims, No Drawings

(56) References Cited

FOREIGN PATENT DOCUMENTS

| JP | 3707758 B2 | 10/2005 | |
|---|---|---|---|
| JP | 2006-057054 A | 3/2006 | |
| JP | 2006-206496 A | 8/2006 | |
| JP | 3963635 B2 | 8/2007 | |
| JP | 2009-209139 A | 9/2009 | |
| JP | 2010-163375 A | 7/2010 | |
| JP | EP 2266532 A2 * | 12/2010 | ............ A61K 8/895 |
| JP | 2011-001332 A | 1/2011 | |
| JP | 2011-011988 A | 1/2011 | |
| JP | 2012-197265 A | 10/2012 | |

OTHER PUBLICATIONS

Mar. 29, 2016 Search Report issued in European Patent Application No. 12891123.7.
Nov. 13, 2015 Arguments to Reasons for Rejection in Japanese Patent Application No. JP-2014-553882.
Jul. 28, 2016 Office Action Issued in U.S Appl. No. 14/424,226.
Jan. 18, 2016 Reasons for Rejection issued in Japanese Patent Application No. 2014-553883.
May 19, 2016 Office Action issued in Japanese Patent Application No. 2016-022292.
May 18, 2016 Invitation Pursuant to Rule 63(1) EPC issued in European Patent Application No. 12 891 116.1.
Jul. 13, 2016 Response to Invitation Pursuant to Rule 63(1) EPC (dated May 18, 2016) issued in European Patent Application No. 12 891 116.1-1458 based on PCT/2012/008346.
May 19, 2016 Reasons for Rejection issued in Japanese Patent Application No. 2016-022291.
Jan. 18, 2016 Reasons for Rejection issued in Japanese Patent Application No. 2014-553882.
Apr. 15, 2016 Communication pursuant to Rules 70(2) and 70a(2) EPC issued in European Patent Application No. 12891123.7.
Sep. 26, 2016 Extended European Search Report issued in Application No. 12891116.1.
Barrere, M. "Anionic Polymerization of Octamethylcyclotetrasiloxane in Miniemulsion II. Molar Mass Analyses and Mechanism Scheme." Polymer, Elsevier Science Publishers B.V, GB, vol. 42, No. 17, Aug. 1, 2001, pp. 7239-7246.
Wikipedia, free encyclopedia. "Shore Durameter." Aug. 2, 2016, XP055294993, URL:https://en.wikipedia.org/w/windex. php?title=Shore_durometer&printable=yes[retrieved on Aug. 11, 2016].

* cited by examiner

SURFACE-TREATED POWDERS AND COSMETIC COMPOSITIONS IN WHICH SUCH POWDERS ARE MIXED

TECHNICAL FIELD

The present invention relates to cosmetic powders in which powders for cosmetics are surface-treated with a silicone gel, and cosmetic compositions containing such powders. Since the treated powders for cosmetics are good in water repellency, and smooth with light touch, moist feeling and excellent adhesion to skin, cosmetic compositions containing such powders have excellent usability, cosmetic effects and cosmetic tenacity with good stability of the cosmetic compositions with lapse of time.

BACKGROUND TECHNIQUES

In order to prevent makeup deterioration with sweat, powders to be mixed into makeup cosmetic compositions such as foundation, eye shadow and mascara are required to have water repellency against sweat. In addition, in order to defend from ultraviolet rays, finely powdery zinc oxide, titanium dioxide, cerium oxide or iron oxide is incorporated as ultraviolet control agents into sun care products. Meanwhile, in order to give water repellency and water proof and improve usability and adhesion to skin as sun screen cosmetics, a powder surface-treated with a silicone compound, a fatty acid, an amino acid or the like are mixed thereinto.

Conventionally, there have been a number of publicly known methods regarding water-repellency treatments of hydrophilic powders to be used in cosmetics, and particularly, utilization of water repellency of silicone compounds has been already well known. For example, disclosure is made of a method in which after a mineral powder such as talc or the like is simply adhered with a silicone compound having hydrogen atoms to directly bond with the powder by mixing in a mixer, the water repellency is given to the mixture by baking under heating; and a method in which silicone treatment is effected by using a silane coupling agent such as dimethyl polysiloxy silazane, trialkoxy polydimethyl siloxane or the like (Patent documents 1, 2, 3).

In addition, recently, many makeup cosmetics such as foundations in which much powders are mixed, stick to slipping property and usability when coated or sprayed on the skins. As compared with conventional products, speadability, slipping property, and adhesionability are improved with lighter touch, and there are observed many cosmetics which are felt comfortable when putting on makeup. Usability and skin adhesion are in a trade-off relationship, and there are not cosmetics which satisfy both of these properties. The powders aiming at the improvement of the slipping property and the usability include spherical ones such as silica beads, alumina beads, nylon powder, PMMA, polyurethane, silicone rubber powder, silicone resin-coated silicone powder, silicone elastomer powder and the like; ones having flattened particle shapes such as hexagonal-crystalline boron nitride, lauroyl lysine, sheet-like barium sulfate, cleavable talc, mica synthesized by wet crushing, sheet-like PMMA, sheet-like cellulose and the like have been developed. Even if these powders are subjected to the above publicly known surface treatment, usability and adhesion to skin are not both improved to satisfactory levels. Besides the powders, other touch improvers include partially crosslinked organopolysiloxanes, represented by KSG-15 (manufactured by Shin-Etsu Chemical Co., Ltd.) in which dimethicone having an Si—H group and vinyl dimethicone are subjected to an addition reaction (Patent Documents 4, 5 and 6). They are in the form of a silicone gel or a silicone elastomer, and are compositions which exhibit the gel property by mixing them with a low-viscosity silicone oil or a low-molecular oil. As the surface-treated powders, soft-touch powders in which surfaces of a scale-like inorganic particles having good adhesion to skin are coated with a resin, and a powder coated with a silicone elastomer to obtain usability with good slip property of the silicone elastomer are disclosed (Patent documents 7, 8, 9 and 10). Silicone elastomer-coated powder having insufficient water repellency is not only obtained, but also many untreated portions of the surfaces of the powder particles are formed on surfaces of powder particles, because the powder has strong agglomeration and they are agglomerated when the powder particles are coated. As a result, such a coated powder has unfavorably undesirable usability and deteriorated adhesion to skin.

As mentioned above, surface-treated powders having good water repellency, smooth and light touch and moist feeling with excellent skin adherability are unavailable, cosmetics having these techniques combined together were yet satisfactory. Moreover, a powder surface-treated with a silicone gel has not been concretely exemplified.

PRIOR ART DOCUMENTS

Patent Documents

Patent document 1: JP-B S45-2915
Patent document 2: JP-B 3079395
Patent document 3: JP-A 2006-206496
Patent document 4: JP-A S63-152308
Patent document 5: JP-B H08-6035
Patent document 6: JP-B 2582275
Patent document 7: JP-B 3963635
Patent document 8: JP-B 3707758
Patent document 9: JP-A 2010-163375
Patent document 10: JP-B 2011-1332

SUMMARY OF THE INVENTION

Problems to be Solved by the Invention

As mentioned above, the heretofore proposed techniques could not produce a powder surface-treated with silicone a compound, which satisfied good water repellency, light usability, moist feeling and adherability to skin. The present invention is to provide a powder having slip property, light touch, moist feeling and excellent adherability to skin, a producing method thereof, and a cosmetic composition containing it.

Measure to Solve the Problems

Having strenuously examined to accomplish the above-mentioned objects, the present inventor has come to know that powders having usability with moist feeling peculiar to silicone gel and excellent adherability to skin can be provided by surface-treating powders for cosmetics with a silicone gel, while good water repellency and smooth and light touch are exhibited, and cosmetic compositions mixed with such powders have excellent usability, cosmetic effects and makeup durability with good stability of the cosmetic compositions with lapse of time. The prevent invention has been accomplished based on the above knowledge.

The present invention relates to a cosmetic powder surface-treated with the following silicone gel, a producing method thereof, and a cosmetic composition containing the surface-treated powder for cosmetic.

[1] A cosmetic powder surface-treated with a silicon gel.

[2] A method for producing the cosmetic powder surface-treated with the above silicone gel.

[3] A cosmetic composition containing the cosmetic powder surface-treated with the above silicone gel.

The present invention relates to the cosmetic powder surface-treated with the silicone gel. The following can be recited as preferred embodiments of the cosmetic powder surface-treated with the above silicone gel according to the present invention.

(i) The cosmetic powder according to [1], wherein the powder is an inorganic powder, an organic powder or a composite powder thereof.

(ii) The cosmetic powder surface-treated with the silicone gel set forth in [1] or [i], wherein the silicone gel is one obtained by hydrolyzing and condensing an organopolysiloxane containing at least a diorgano polysiloxane having reactive opposite ends represented by the following formula (1) and either a silane coupling agent of the following formula (2) having at least two hydrolyzable groups per one molecule or a reactive organo polysiloxane having the following formula (3) as a crosslinking agent.

(Chemical formula 1)

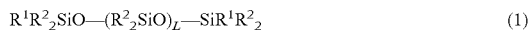

$R^1R^2{}_2SiO\text{—}(R^2{}_2SiO)_L\text{—}SiR^1R^2{}_2$  (1)

($R^1$ is a hydrolyzable group such as a hydroxyl group, an amino group, an acetoxy group, an alkoxy group or a hydrogen atom, $R^2$ is a non-substituted or substituted C1-C20 monovalent hydrocarbon group, and L is 3 to 10,000.)

(Chemical formula 2)

$R^3R^4{}_nSiX_{(3-n)}$  (2)

($R^3$ is a group selected from a C1-C20 monovalent hydrocarbon group, an amino group, an aminoethyl group, a mercapto group, an isocyanate and a phenyl group, $R^4$ is a group selected from a C0-C3 monovalent lower alkyl group and a phenyl group, X is a hydroxyl group or an alkoxy group, and n is 0 or 1).

(Chemical formula 3)

$R^5{}_3SiO\text{—}(R^5{}_2SiO)n\text{-}SiR^5{}_3$  (3)

(R5 is a hydrolyzable group or a non-substituted or substituted C1-C20 monovalent hydrocarbon group, the hydrolyzable group is any of a hydroxyl group, an amino group, an acetoxy group, an alkoxyl group and a hydrogen atom, n is 3 to 1,000, and at least three hydrolyzable groups are provided in one molecule).

(iii) The cosmetic powder set forth in any one of [1] and (i) to (ii), wherein the silicone gel has a complex modulus of 3,000 to 100,000 Pa, and a loss coefficient tan δ is 1.0 to 2.5 in measurement of a dynamic viscoelasticity under a distortion factor of 17% at 25° C. and a shear frequency of 4 Hz.

(iv) The cosmetic powder set forth in any of [1] and (i) to (iii), wherein the diorganopolysiloxane of the formula (1) is a dimethiconol.

(v) The cosmetic powder set forth in (iv), wherein a water emulsion obtained by mechanically emulsifying the dimethiconol having a number of dimethyl siloxane units L of 3 to 1,000 in the formula (1) is used as a starting material for the surface treatment.

(vi) The cosmetic powder set forth in (iv), wherein a water emulsion obtained by emulsion polymerizing the dimethiconol having a number of dimethyl siloxane units L of 3 to 1,000 in the formula (1) is used as a starting material for the surface treatment.

(vii) The cosmetic powder set forth in (iv), wherein a water emulsion of the dimethiconol obtained by emulsion polymerizing octamethyl cyclotetrasiloxane as a starting material is used as a starting material for the surface treatment.

(vii) The cosmetic powder set forth in (iv), wherein a water emulsion of the dimethiconol obtained by emulsion polymerizing octamethyl cyclotetrasiloxane as a starting material is used as a starting material for the surface treatment.

(viii) The cosmetic powder set forth in any of (v) to (vii), wherein a surface active agent contained in the water emulsion of the dimethiconol includes at least an acylated amino acid.

(ix) The cosmetic powder set forth in any of (v) to (viii), wherein a mixing weight ratio (B)/(A)×100 between the weight (B) of the surface active agent and that (A) of the dimethiconol in the water emulsion of the dimethiconol is less than 6.0.

(x) The cosmetic powder set forth in any of [I] and (i) to (ix), wherein the organic group R3 of the silane coupling agent of the formula (2) is either an amino group or a phenyl group.

(xi) The cosmetic powder set forth in any of [1] and (i) to (x), wherein a mixing weight ratio between the silicone gel and the cosmetic powder is 100/0.1 to 100/25.0.

(xii) The cosmetic composition set forth in any of [1] and (i) to (xi), which is obtained by hydrolyzing and condensing at least partially the diorgano polysiloxane of the above (1) having the reactive opposite ends and the silane coupling agent of the above (2) or the organo polysiloxane of the above (3) in the presence of the cosmetic powder in a state that a mixed state of a water-soluble solvent and the cosmetic powder is in either a capillary or slurry state, in a step of separately adding or simultaneously adding the diorgano polysiloxane and the silane coupling agent or the organo polysiloxane.

(xiii) A cosmetic composition containing 0.1 wt % or more of the cosmetic powder surface-treated with the silicone gel set forth in any of [1] and (i) to (xii).

Effects of the Invention

The cosmetic powder according to the present invention is a powder that has good water repellency, can exhibit smooth and light touch, moist usability peculiar to the silicone gel, and is excellent in adhesion to skin. The cosmetic composition into which the powder is mixed has excellent cosmetic effects, excellent cosmetic-lasting quality and good stability with lapse of time can be provided.

Embodiments to Carry Out the Invention

In the following, [1] the cosmetic powder surface-treated with the silicone gel, [2] the method for producing the cosmetic powder surface-treated with the silicone gel, and [3] the cosmetic composition containing the powder for cosmetics surface-treated with the above silicone gel will be explained in this order with respect to the present invention.

[1] Cosmetic Powder Surface-Treated with the Silicone Gel

The cosmetic powder according to the present invention is a powder surface-treated with a silicone gel, preferably a surface-treated powder which is surface-treated with the silicone gel, using a water emulsion of dimethiconol.

(Cosmetic Powder)

The surface-treated powder according to the present invention is a powder for cosmetics to be incorporated into a cosmetic composition. The cosmetic powder may be any of an inorganic powder, an organic powder or an inorganic/inorganic composite powder, an inorganic/organic composite powder or an organic/organic composite powder, and only one kind may be used or two or more kinds thereof may be used in an appropriately combined manner. Such a cosmetic powder has safety for human bodies and skins, and powders capable of being substantially used for the cosmetic compositions and powders having particle diameters in the entire range can be used. In addition, any shapes including spherical shapes, semi-spherical shapes, star-like shapes, polyhedron shapes, spindle shapes, needle shapes, plate-like shapes and the like may be used, so long as the geometric shapes are used in the ordinary cosmetic compositions. Further, the cosmetic powders may be non-porous or porous.

The average particle diameter is preferably in a range of 0.01 to 500 μm, more preferably 0.1 to 100 μm. If the particle diameters are smaller than 0.01 μm, the powder is strongly agglomerated with the silicone gel, so that usability and light touch may be deteriorated. On the other hand, if they are more than 500 μm, physical surface roughness is large, so that improvement of slipping property cannot be expected. The average particle diameters are measured by appropriately selecting an appropriate principle of a microscopic method, a light scattering method, a laser diffraction method, a liquid phase precipitation method, an electric resistance method and the like, depending upon the respective shapes of the powder particles.

For example, as the inorganic powders, recitation is made of sericite, natural mica, fired mica, synthetic mica, synthetic sericite, alumina, mica, talc, kaolin, bentonite, smectite, montmorilonite, hectorite, zeolite, calcium carbonate, magnesium carbonate, anhydrous silicic acid, magnesium silicate, aluminum silicate, aluminum magnesium silicate, calcium silicate, barium silicate, strontium silicate, calcium phosphate, magnesium oxide, barium sulfate, magnesium metasilicate aluminate, iron oxide, chromium oxide, titanium oxide, zinc oxide, cerium oxide, aluminum oxide, magnesium oxide, chromium hydroxide, iron blue, ultramarine blue, calcium carbonate, magnesium carbonate, calcium phosphate, aluminum hydroxide, barium sulfate, magnesium sulfate, silicon carbide, metal tungstate, magnesium aluminate, magnesium methasilicate aluminate, chlorohydroxy aluminum, clay, hydroxy apatite, ceramic powder, boron nitride, aluminum nitride, titanium nitride, silicon nitride, silicone carbamate, cobalt titanate, iron titanate, lithium cobalt titanate, cobalt aluminate, inorganic blue pigment, aluminum powder, gold powder, silver powder, iron powder, platinum powder, butterfly-shaped barium sulfate, flower petal-shaped zinc oxide, tetrapod-shaped zinc oxide, and finely particulate zinc oxide, titanium oxide-coated mica, titanium oxide-coated mica, titanium oxide-coated synthetic mica, bismuth oxychloride, titanium oxide-coated talc, argentine, titanium oxide-coated colored mica, titanium oxide-coated borosilicic acid (sodium/calcium), titanium oxide-coated borosilicic acid (calcium/aluminum), zinc oxide-coated talc, zinc oxide-coated mica, zinc oxide-coated silica, colcothar-coated mica, colcothar-coated titanium mica, colcothar/black iron oxide-coated titanium mica, carmine-coated titanium mica, carmine/indigo blue-coated titanium mica, stainless powder, copper powder, tourmaline powder, mango violet, cobalt violet, glass fibers, carbon fibers, silicon carbide fibers, alumina fibers, β-wollastonite, β, zonolite, potassium titanate fibers, aluminum borate fibers, basic magnesium sulfate fibers, silicon nitride fibers, etc., metal tungstate, metallic powder pigments such as aluminum powder, copper powder, stainless powder, etc.

These powders may be used singly or in combination. For example, a composite powder in which surfaces of mica particles or surfaces of pearl particles are combined with aluminum hydroxide (Excel mica JP-2, Excel pearl: Miyoshi Kasei, Inc.), a powder in which hydroxy apatite and zinc oxide are fixed on surfaces of sericite particles in combination (Powder Lavie: Miyoshi Kasei, Inc.), a powder in which surfaces of mica particles are combined with silica beads (SXI-5: Miyoshi Kasei, Inc.), and a powder in which surfaces of mica or talc particles are combined with titanium oxide or finely particulate titanium oxide (TMC series or TTC series: Miyoshi Kasei, Ltd.) and the like are recited.

As organic powders, for example, recitation is made of polyamide, polyacrylic acid and acrylic acid esters, polyester, polyethylene, polypropylene, polystyrene, styrene-acrylic acid copolymer, divinylbenzene/styrene copolymer, polyuretane, vinyl resin, urea resin, melamine resin, benzoguanamine, polymethyl benzoguanamine, polyethylene terephthalate, methyl polymethacrylate, polymethylmethacrylate, etc., polymethyl methacrylate, cellulose, silk, phenol resin, epoxy resin, polycarbonate, a silicone resin powder, silicone rubber powder, fluorine resin powders such as a Teflon (trademark) powder, etc., metal soaps such as zinc stearate, aluminum stearate, calcium stearate, magnesium stearate, zinc myristate, magnesium myristate, zinc cetyl phosphate, calcium cetyl phosphate, zinc sodium cetyl phosphate, etc., lauroyllysine, alkylphospholic acid, chitin, chitosan, polysaccharide powder, protein powder, carbon black and further organic colorants. As the tar dye, recitation is made of Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207, etc.; and natural colorants such as carminic acid, laccaic acid, carthamine, brazilin, crosin, etc.

In addition, in order to improve affinity and firm adhesion with the surface-treating agent, the powder to be surface-treated in the present invention may be coated with an oxide or a hydrous oxide of at least one kind of aluminum, calcium, magnesium, cerium, silicon, zirconia, titanium, zinc, iron, cobalt, manganese, nickel and tin, for example.

Method for Producing Silicone Gel

The silicone gel referred to in the present invention is one obtained from a curable liquid silicone composition, its curing is effected by an addition reaction or a condensation reaction. As for the addition reaction, recitation is made of for example, a silicone gel obtained by an addition reaction between an organo polysiloxane having at least two monovalent olefinic unsaturated groups in one molecule and an organo hydrogen polysiloxane having at least three hydrogen atoms bonded to silicon atoms in one molecule under a platinum-based catalyst. As for the condensation reaction, recitation is made of a silicone gel obtained by condensation polymerizing a liquid silicone composition composed of an organo polysiloxane having at least two hydroxy groups bonded to silicon groups in one molecule and an organo hydrogen polysiloxane having at least three hydrogens bonded to silicon atoms in one molecule, in the presence of a condensation catalyst. A preferred method for obtaining the silicone gel in the present invention is one using the condensation reaction. A preferred embodiment is a polymer with a finely 3-dimensional crosslinked structure of a diorgano polysiloxane obtained by hyrolyzing and condensing an organopolysiloxane containing at least a diorganopolysiloxane having reactive opposite ends represented by the following formula (1) and either silane coupling agent having two or more hydrolyzable groups in one molecule represented by the following formula (2) or a reactive organopolysiloxane having the following formula (3) as a crosslinking agent.

(Chemical formula 1)

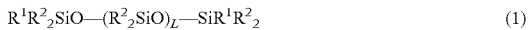

$R^1R^2{}_2SiO\text{—}(R^2{}_2SiO)_L\text{—}SiR^1R^2{}_2$ (1)

($R^1$ is a hydrolyzable group such as a hydroxyl group, an amino group, an acetoxy group, an alkoxy group or a hydrogen atom, $R^2$ is a non-substituted or substituted C1-C20 monovalent hydrocarbon group, and L is 3 to 10,000.)

(Chemical formula 2)

$R^3R^4{}_nSiX_{(3-n)}$ (2)

($R^3$ is a group selected from a C1-C20 monovalent hydrocarbon group, an amino group, an aminoethyl group, a mercapto group, an isocyanate and a phenyl group, $R^4$ is a group selected from a phenyl group or a C0-C3 monovalent lower alkyl group and a phenyl group, X is a hydroxyl group or an alkoxy group, and n is 0 or 1).

(Chemical formula 3)

$R^5{}_3SiO\text{—}(R^5{}_2SiO)n\text{-}SiR^5{}_3$ (3)

($R^5$ is a hydrolyzable group or a non-substituted or substituted C1-C20 monovalent hydrocarbon group, the hydrolyzable group is a hydroxyl group, an amino group, an acetoxy group, an alkoxyl group or a hydrogen atom, n is 3 to 1,000, and at least three hydrolyzable groups are provided in one molecule).

Here, as R2 in the formula, recitation is made of for example, alkyl groups such as a methyl group, an ethyl group, and a proply group, a butyl group, a pentyl group, or a hexyl group, a heptyl group, an octyl group, a nonyl group, a decyl group, an undecyl group, a dodecyl group, a tetradecyl group, a pentadecyl group, a hexadecyl group, a heptadecyl group, an octadecyl group, a nonadecyl group, an eicosyl group, a henicosyl group, a dodecyl group, a tricosyl group, a tetrasyl group, and a triacotyl group; cycloalkyl groups such as a cyclobutyl group, a cyclopentyl group, a cyclohexyl group, and a cycloheptyl group; aryl groups such as a phenyl group, a tolyl group and a naphthyl group; aralkyl groups such as a benzyl group, a phenethyl group, and a β-phenylpropyl group; and hydrocarbons in which a part or an entire part of hydrogen atoms bonded to carbon atoms of these groups are replaced by atoms such as halogen atoms (fluorine atoms, chlorine atoms, bromine atoms or iodine atoms) and/or substituent groups such as an acryloyloxy group, a methacryloyloxy group, an epoxy group, a glycidoxy group, an amino group, a mercapto group or a carboxyl group.

Different from silicone elastomer, the silicone gel to treat the surface to be surface-treated takes the form of particles instead of elastic solid. In this case, the surface treatment may be effected for any shape of the silicone gel. The surface treatment referred to in the present invention means a state in which surfaces of the powdery particles are attached or coated with the silicone gel. The density or the shape of the silicone gel attached onto the surfaces of the powdery particles is not particularly limited, so long as the effects to be accomplished by the present invention are exhibited. That is, it may be that the particulate silicone gel is sparsely attached to the surfaces of the powders, or the surfaces of the powdery particles are coated and attached with the particulate silicone gel without gaps, or the non-particulate silicone gel are sparsely attached to the surfaces of the powdery particles, or the surfaces of the powder particles are coated and attached with the silicon gel in the filmy form without gaps. It may be that the above states are combined together.

For example, one kind of appropriate finely crosslinking reaction systems of the silicone to obtain the silicone gas as referred to in the present invention is accompanied with a condensation reaction between a silanol (≡Si—OH) group and a silicon hydride (≡Si—H), a condensation reaction between a silanol (≡Si—OH) group and a hydrolyzable or condensable silyl group, that is, ≡SiOR (alkoxy group), ≡Si—OC(O)CH3, ≡Si—NR2 and ≡Si—ON═CR2, a condensation reaction between silicon hydride and a hydrolyzable or condensable group, and a condensation reaction between two same or different hydrolyzable or condensable groups.

As one example of these finely crosslinking reaction system, a reaction is effected between a siloxane polymer having silanol groups and a crosslinkable compound having hydrolysable groups directly bonded to silicon atoms. As another example of this reaction system, a reaction is effected between a siloxane polymer having hydrolysable or condensable groups directly bonded to silicon atoms and a crosslinkable compound having a silanol group. As a further example of the above curing system, a reaction is effected between two siloxane polymers having hydrolysable or condensable groups directly bonded to silicon atoms. As a still further example of the above curing system, a reaction is effected between a siloxane polymer having hydrolysable or condensable groups directly bonded to silicon atoms and a siloxane polymer having a group with an active hydrogen atom, that is, a hydroxy group, a ureide group, a mercapto group or an amino group.

The most preferable kind of the finely crosslinking reaction system in the present invention is a condensation reaction between a hydroxysilyl group (≡SiOH) and an ethoxysilyl group (≡SiOCH2CH3), between a hydroxysilyl group (≡SiOH) and a methoxysilyl group (≡SiOCH3), between a hydroxysilyl group (≡SiOH) and a hydrosilyl group (≡SiH) or the like.

When the silicone gel is obtained by condensation reaction as a preferable finely crosslinking reaction system in a condensation reaction in the present invention, the diorganopolysiloxane with the reactive opposite ends shown in the above formula (1), the silane coupling agent shown in the above formula (2) and/or the reactive organopolysiloxane having at least three hydrolyzable groups per one molecule shown in the above formula (3) can be selected from among the following ones.

As the diorganopolysiloxane with the reactive opposite ends shown in the above formula (1), recitation is made of silicone modified at opposite ends with hydroxysilyl groups, or methoxy group, or ethoxy groups, or amino groups, or hydroxysilyl groups at opposite ends. As generally available ones, recitation is made of silicones modified at opposite ends with hydroxysilyl groups such as X-21-5849, X-21-

5841, KF-9701A (Shin-Etsu Chemical Co., Ltd.), FINISH WS 62M, CT601M, CT5000M, CT6000M (Asahi Kasei Waker Silicone Co., Ltd.), and silicones modified at opposite ends with amino groups, such as KF8010, X-22-161A, KF8008 (Shin-Etsu Chemical Co., Ltd.), etc. As a preferred diorganopolysiloxane with reactive opposite ends according to the present invention, a silicone (dimethiconol) modified at opposite ends with hydroxysilyl groups that produces water as a byproduct after hydrolysis and condensation reaction is recited.

As examples of the silane coupling agent shown by the above formula (2), recitation is made of dimethyldimethoxysilane, methyltrimethoxysilane, dim ethyldiethoxysilane, methyltriethoxysilane, diphenyldiethoxysilane, phenyltriethoxysilane, 3-glycidoxypropyltriethoxysilane, 5,6-epoxyhexyltriethoxysilane, 2-(3,4-epoxycyclohexyl)ethyltriethoxysilane, 3-acryloxypropyltriethoxysilane, 3-methacryloxypropyltriethoxysilane, N-(2-aminoethyl)-3-amonopropyltriethoxysilane, 3-aminopropyltriethoxysilane, 3-mercaptopropylmethyldiethoxysilane, n-octyltriethoxysilane and the like. However, it is not limited to them, and a mixture of two or more kinds of them can be used depending upon a purpose.

As examples of the reactive organopolysiloxane having at least three hydrolyzable groups per one molecule shown in the above formula (3), recitation is made of α-trihydroxydimethylpolysiloxane, α-trialkoxypolydimethylsiloxane, α,ω-dialkoxypolydomethylsiloxane, α,ω-hexaalkoxypolydimethylsiloane, dimethyl hyrogen polyiloxane, triethoxysilylethylpolydimethylsiloxyethyl dimethicon, triethoxysilylethylpolydimethylsiloxyethylhexyl dimethicone and the like. However, it is not limited to them, and a mixture of two or more kinds of them can be used depending upon a purpose.

The most preferable finely crosslinking reaction system in the present invention is a silicone gel in which the above crosslinking agent is reacted with the diorganopolysiloxane having the reactive opposite ends of the above formula (1) in the form of a water suspension or a water emulsion as a starting material. As a method for preparing a water emulsion of the diorganopolysiloxane having the above formula (1) with the reactive opposite ends, recitation is made of a method for effecting an emulsion polymerization by using a low-molecular cyclic siloxane as a starting material, or a method for mechanically emulsifying a system containing at least an oily diorganopolysiloxane having reactive opposite ends, a surface active agent and water by an emulsion mixing device. Any kind of mixing devices may be used to effect the emulsifying step. That is, a batch type mixer, a planetary type mixer, a continuous mixer such as a uniaxial or multi-axial screw extruder, a dynamic or static mixer, a colloid mill, a homogenizer or a sonolator or a combination may be used.

An emulsion may be produced by any publicly known method. For example, when a water emulsion of the diorganopolysiloxane having the reactive opposite ends is to be obtained by the mechanical emulsion, however, the method undergoes the limitation of the viscosity of the diorganosiloxane. The unit number of the diorganosiloxane is preferably in a range of 3 to 1,000, As a producing method, the emulsion can be obtained by mixing and emulsifying the diorganopolysiloxane having the reactive opposite ends, the surface active agent and water. The molecular weight of the obtained organopolysiloxane can be known by drying off the water of the emulsion and measuring the Mw of the remainder after the evaporation with GPC in terms of the PS conversion.

As another method, when the water emulsion of the diorganopolysiloxane having the reactive opposite ends is to be obtained by the emulsion polymerization, the water emulsion of the organopolysiloxane containing hydroxy groups bonded to silicon atoms of the opposite ends of the straight-chain molecule can be produced by adding a surface active agent and water to a lower-molecular cyclic cyclohexane or dimethiconol, emulsifying the mixture, and then performing the polymerization reaction through addition of an acid, and neutralizing a product mixture with addition of an alkaline. The molecular weight of the obtained organopolysiloxane can be known by measuring the PS-converted Mw with the GPC in the same manner as mentioned before.

Meanwhile, as another method, a water emulsion of a partially finely crosslinked organopolysiloxane silicone containing hydroxy groups bonded to silicone atoms of the opposite ends can be obtained by adding a fine amount of a crosslinking agent, a surface active agent and water to a lower-molecular cyclic siloxane, emulsifying them, then subjecting them to a polymerization reaction with the addition of an acid, and neutralizing them with the addition of an alkaline.

The surface active agent to be used in emulsifying the water emulsion of the diorganopolysiloxane having the reactive opposite ends is not limited. For example, non-ionic surface active agents such as polyoxyethylene alkyl ether, polyoxyethylene polyoxypropyrene alkyl ether, polyoxyethylene alkylphenyl ether, polyethylene glycol fatty acid ester, sorbitan fatty acid ester, polyoxyethylene sorbitan fatty acid ester, polyoxyethylene sorbit fatty acid ester, glycerin fatty acid ester, polyoxyethylene glycerin fatty acid ester, polyglycerin fatty acid ester, propylene glycol fatty acid ester, polyoxyethylene propylene glycol fatty acid ester, polyoxyethylene castor oil, polyoxyethylene cured castor oil, polyoxyethylene cured castor oil fatty acid ester, polyoxyethylene phytostanol ether, polyoxyethylene phytosterol ether, polyoxyethylene cholestanol ether, polyoxyethylene cholesteryl ether, polyoxyethylene alkyl amine, alkylalkanol amide, sucrose fatty acid ester, methyl glycoside fatty acid ester, alkyl polyglycoside, straight chain-or branched polyoxyethylene-modified organopolysiloxane, straight chain-or branched polyoxyethylene polyoxypropyrene-modified organopolysiloxane, polyoxyethylene.alkyl co-modified organopolysiloxane, straight chain-or branched polyoxyethylenepolyoxypropyrene.alkyl co-modified organopolysiloxane, straight chain-or branched polyglycerin-modified organopolysiloxane, straight chain-or branched polyglycerin.alkyl co-modified organopolysiloxane, polyvinyl alcohol, polyvinyl pyrolidone, methyl cellulose and hydroxypropyl methyl cellulose; anionic surface active agent such as alkyl sulfate, polyoxyethylene alkyl ether sulfate, polyoxyethylene alkylphenyl ether sulfate, a sulfate of a fatty acid alkylolamide, alkylbenzene sulfonate, a polyoxyethylene alkylphenyl ether sulfonate, α-olefinsulfonate, an α-sulfo fatty acid ester salt, alkyl naphthalene sulfonic acid, an alkyldiphenyl ether disulfonate, an alkane sulfonate, N-acyltaurinate, a dialkylsulfosuccinic acid, a monoalkylsulfosuccinate, a polyoxyethylenealkyl ether sulfosuccinate, a fatty acid salt, a polyoxyethylene alkyl ether carboxylate, an N-acylamino acid salt, a monoalkyl phosphate, a dialkyl phosphate, a polyoxyethylene alkyl ether phosphate, a carboxymethyl cellulose, a polyacrylate, a polystyrene sulfate, a naphthalene sulfonate formalin condensate, an aromatic sulfonate formalin condensate, a carboxyvinyl polymer, and a styrene oxyalkylene acid anhydride copolymer; cationic surface active agents such as an alkyltrimethyl ammonium salt, a dialkyldimethyl ammonium salt, a polyoxyethylene alkyl dimethyl ammonium salt, a dipolyoxyethylenealkylmethyl ammonium salt, a tripolyoxyethylenealkyl ammonium salt, an alkylbenzyldimethyl ammonium salt, an alkylpyridium salt, a monoalkylamine salt, a dialkylamine salt, a trialkylamine salt, a monoalkylamideamine salt and a cationic cellulose; amphionic surface active agents such as an alkyldimethylamine oxide, an alkyldimethylcarboxy betaine, an alkyl amide propylmethyl carboxybetaine, an alkylhydroxy sulfobetaine, an alkylcarboxymethyl hydroxyethylimidazolium betaine and the like. These surface active agents can be used singly or by appropriately combining two or more kinds thereof. Preferable surface active agents are less irritating to skins, and not controlled substances by the PRTR law (Pollutant Release and Transfer Register). For example, Na or K salts and the like of a polyether-modified silicone, lauroyl glutamic acid, myristoyl glutamic acid, lauroyl asparaginic acid, myristoyl asparaginic acid, lauroyl alanine, lauroylmethyl taurine, myristoylmethyl taurine and the like are recited, and one or more kinds thereof can be mixed.

When a water emulsion of a diorganopolysiloxane with reactive opposite ends is used as a starting material to obtain a silicone gel referred to in the present invention, the surface active agent contained in the water emulsion is preferably as small as possible from the standpoint that it gives water repellency to the surface-treated powder and it remains due to adsorption in the powder. The mixing weight ratio (B)/(A)×100 is preferably less than 6.0 in which (A) is the amount of the organopolysiloxane with the reactive opposite ends and (B) is that of the surface active agent. If the weight ratio is 6.0 or more, the water repellency of the surface-treated powder may be lowered, or no light touch may be obtained.

The mixing ratio between the diorganopolysiloxane with the reactive opposite ends and the crosslinking agent and the number of the reactive groups are determined depending upon whether the silicone gel is obtained by the finely crosslinking reaction or not. In general, when the sum of the number of the reactive groups of the reactive diorganopolysiloxane and that of the reactive groups of the crosslinking is at least 5, a structural material in the form of a silicone elastomer is formed by a crosslinking reaction. If both of the molecular weight of the diorganopolysiloxane with the reactive opposite ends and that of the crosslinking agent are small, although not generally said because the obtained silicone polymer is a solid elastic body, the ratio of the diorganopolysiloxane with the reactive opposite ends and the crosslinking agent in the silicone gel according to the present invention is almost in a mixed ratio of 100/0.1 to 100/35 (wt %). If the amount of the crosslinking agent is less than 0.1 wt %, the product is a viscous silicone oil or gum, whereas if it is more than 35 wt %, the product is a silicone elastomer having elasticity to lower the water repellency of the surface-treated powder.

When the diorganopolysiloxane with the reactive opposite ends and the crosslinking agent are to be finely crosslinked, a catalyst to invoke the reaction may be added. As a preferably appropriate catalyst, an acidic substance or an alkaline substance is recited. The acidic substance is not particularly limited, and for example, organic acids such as lactic acid, citric acid, malic acid, succinic acid and the like, hydrochloric acid, sulfuric acid, phosphoric acid, aluminum chloride, zinc chloride, magnesium chloride, polyaluminum chloride, aluminum sulfate, zinc sulfate and the like can be used.

The alkaline substance is not particularly limited, and for example, alkaline metal hydroxides such as potassium hydroxide, sodium hydroxide, lithium hydroxide and the like; alkali earth metal hydroxides such as calcium hydroxide, magnesium hydroxide, barium hydroxide and the like; alkali metal carbonates such as potassium carbonate, sodium carbonate and the like; ammonia, triethanolamine and the like can be used. In the present invention, as to the silicone gel, a compound composed mainly of a silicone having no rubbery elasticity is good. Generally, in case of the dimethylpolysiloxane, if the number of linear siloxane units is small, that is, if the molecular weight becomes small, the product is volatile. As the molecular weight increases, the product is from liquid, viscous liquid to gum. When a molecular crosslinking agent is added to the dimethylpolysiloxane chains having a linear molecular structure, the product changes from a gel, an elastic material to a resinous material with increase in the addition amount thereof.

The amount of the silicone gel to be used as a coating material for the surface treatment in the present invention differs depending upon the kind of the powder used and a coating method, and is not particularly limited. The ratio between the powder and the silicone gel as the surface treating agent is that the powder: the silicone gel is preferably 99.99:0.01 to 70:30, particularly preferably 99:1 to 90:10. When the ratio is in the above range, the cosmetic powder according to the present invention being smooth and light touch with moist feeling and excellent adhesion to skin can be obtained.

The silicone gel referred to in the present invention is a polymer having a finely three-dimensional crosslinking structure of the diorganopolysiloxane without rubbery elasticity or rubber hardness. In order to specify the silicone gel in the present invention, a measuring method is available, in which the rubber hardness is measured by a durometer specified by ISO7619-1. As this measuring method, a measuring method with Durometer type AO which is capable of measuring the soft rubber hardness is available. A preferable measurement value of the silicone gel in the present invention is less than 10, more preferable less than 5, and further preferably 0.

Further, the silicone gel is used in the present invention, in which rheological properties of the silicone gel includes a complex modulus of 3,000 to 100,000 Pa, and a loss coefficient tan δ is 1.0 to 2.5 in measurement of a dynamic viscoelasticity under a distortion factor of 17% at 25° C. and a shear frequency of 4 Hz. More preferably, a complex modulus is 10,000 to 100,000 Pa, a loss coefficient (loss elasticity G"/storage elasticity G') tan δ is 1.0 to 2.0. If the complex modulus is less than 3,000 pa, the silicon gel exhibits the property of the silicone oil, which does not afford the usability in the present invention. If the complex modulus is more than 100,000, the product exhibits the elastic body, which tends to deteriorate the water repellency and adhesion to skin. If the loss coefficient tan δ is less than 1.0, the product exhibits the properties of the elastic body, which tends to deteriorate the water repellency and adherence to skin. If the loss coefficient tan δ is more than 2.5, the product exhibits the properties of the silicone oil, which does not afford the usability in the present invention. The reason why the shear frequency is set at 4 Hz is that it is in a range of a physically moving speed general to human beings, which is near to a speed at which a cosmetic composition is applied to skin. The rheological properties of the silicone gel in the present invention can be measured as follows. Measurement is carried out in an automatically measuring mode by a dynamic viscoelasticity measuring device: Rheosol-G3000 (manufactured by UBM Co., Ltd.) under a measuring jig: parallel plates in a diameter of 20 mm, a measuring frequency: 4 Hz, measuring temperature: 25±1.0° C., setting of measuring distortion: a distortion rate 17% being set, and a thickness of a measuring sample (gap): 1.0 mm.

As to a method of preparing samples in the measurement of the rubber hardness and the measurement of the dynamic viscoelasticity in the silicone gel, such samples can be obtained as residues through evaporation of water under heating after the diorganopolysiloxane having the reactive opposite ends is emulsified in ion-exchanged water with a surface active agent, a crosslinking agent is added thereto and pH of the mixture is adjusted to basic.

[2] Method for Producing Silicone Gel Cosmetic Powders

The cosmetic powder coated with the silicone gel according to the present invention can be produced by simply mixing and treating the cosmetic powder with the silicone gel by a mixer or the like. Since the silicone gel firmly agglomerates the powder particles together, it is preferable that mixing is carried out by using an organic solvent with a lower surface tension in combination from the standpoint of the water repellency, usability and adhesion to the skins. As a more preferable method for producing the silicone gel-treated powder according to the present invention, after the silicone gel is deposited on the surfaces of the powder particles in the presence of the cosmetic powder by an in-situ method, the treated powder can be obtained by fixing the silicone gel onto the surfaces of the particles under heating. As a further preferable method, a water emulsion of the organopolysiloxane with the reactive opposite ends is used as a starting material, and the silicone gel is fixed by the above in-situ method. This method enhances the uniform attachment and coating of the silicone gel onto the surfaces of the powder particles, so that water repellency is improved and good and lighter usability can be afforded. Thereby, the excellent silicone gel cosmetic powder can be obtained due to the adherence to the skins.

According to the method for producing the cosmetic powder surface-treated with the silicone gel in the present invention, in a step in which the diorganopolysiloxane of the above (1) having the reactive opposite ends and the compound in the above (2) or the above (3) are separately or simultaneously added in the presence of the cosmetic powder in a state that a mixing state of the water soluble solvent and the powder for cosmetics is in a capillary or slurry state, at least a part of the mixture is hydrolyzed and condensed, and thereafter the surface-treated powder is obtained by heating at an internal temperature of 100 to 180° C. for 3 hours or more. More specifically, although different depending upon the particle diameters, the specific surface area and the absorbed water of the powder, the water soluble component is preferably in an amount of 3 to 1500 mass parts, more preferably 10 to 800 mass parts relative to 100 mass parts of the powder for cosmetics. If the water soluble component is less than 3 mass parts, the mixture is not in the capillary state but in a dry mixed state, so that the powder particles are agglomerated to deteriorate the usability. If the water soluble component is unfavorably more than 1500 mass parts, the productivity of the surface-treated powder is deteriorated to increase the production cost.

The mixing state of the powder and the liquid as referred to in the present invention means that although as a packed state among solid, liquid and gas, there are (a) a dry state in which a solid phase and a gas phase continue, and almost no liquid phase exists; (b) a pendular state in which the solid phase and the gas phase are continuous, and the liquid phase is discontinuous; (c) a funicular state in which the solid phase, the gas phase and the liquid phase are continuous: (d) a capillary state in which the solid state is discontinuous, while the liquid is continuous but does not flow; and (e) a slurry state in which the solid phase is discontinuous and the liquid is continuous and flows, and the hydrolysis and the condensation reaction is preferably carried out in the state (d) or (e) among them, while the mixture is being mixed, kneaded or stirred.

The water-soluble solvent refers to any of water, ethanol and ispropyl alcohol (IPA) and a mixed solvent thereof. Water is preferable as the water-soluble solvent from the standpoint of the environment and the cost, and ethanol or IPA can be used as a washing solvent when a compound produced as a byproduct in a reaction process, the surface active agent and the like are to be removed.

As the producing method in the capillary state, for example, after the cosmetic powder, the water-soluble solvent and the diorganopolysiloxane having the reactive opposite ends are well kneaded in a kneader, the crosslinking agent is gradually added thereto under kneading, and if necessary, an acidic material or an alkaline material is added as a reaction catalyst, followed by further kneading for a given time. After the kneaded mixture is taken out, the mixture is heated at a temperature of 100 to 180° C. in a hot gas dryer for 3 hours or more with an internal temperature being a preset temperature, and then cooled and crushed to obtain the powder surface-treated with the silicone gel. Although dimethiconol may be in an oily form or a water-emulsion form at that time, the water emulsion is preferably used from the standpoint of the water repellency.

As a producing method in the slurry state, for example, the cosmetic powder is fed into a water soluble solvent, which is dispersed in a stirrer. After a water emulsion of the diorganopolysiloxane with the reactive opposite ends is gradually added under stirring and the mixture becomes homogeneous, a crosslinking agent is gradually added, which is further stirred, and if necessary, an acidic material or an alkaline material is added thereto as a reaction catalyst, followed by stirring for a given time period. As the condensation reaction proceeds, the slurry liquid becomes viscous, so that the mixture is stirred for a given time. The liquid is removed from the resultant by filtration or a centrifugal separator, which is washed and liquid-removed if necessary. After the cake is heated at a temperature of 100 to 180° C. by a hot gas dryer for 3 hours or more with an internal temperature being at a preset temperature, the resultant is cooled and crushed to obtain the powder treated with the silicone gel. Separation of the solid and the liquid can be carried out at this time by heating under ordinary pressure or reduced pressure. More specifically, a method in which water is removed by keeping still the dispersion liquid under heating, a method in which water is removed by flowing the dispersion liquid under stirring and heating, a method in which the dispersion liquid is sprayed and dispersed in a hot gas stream as in a flush dryer, a spray dryer or the like, and a method utilizing a fluidizing heat medium are recited, for example.

In the producing method in the capillary state or the slurry state, the adding order of the diorganopolysiloxane with the reactive opposite ends, the crosslinking agent and the reaction catalyst is set such that the effects of the present invention may be obtained to a largest extent depending upon the kind of the powder. They may be separately or simultaneously added.

As to the kneading and the stirring in the above producing methods, strong kneading and stirring are preferable, because the powder particles can be homogeneously surface-treated, and a kneader, a biaxial kneader, a disperser mixer, a homomixer and the like are recited.

The temperature in the surface treatment is preferably 5 to 60° C., and more preferably 15 to 30° C. If this temperature is less than 5° C., the hydrolysis and condensation reaction is less likely to proceed, so that the intended effects cannot be obtained, whereas if the temperature is more than 60° C., the obtained particles are strongly agglomerated, so that the usability is deteriorated.

The dried powder may be crushed or classified by a crushing device such as a pin mill, a hammer mill, a jet mill, a ball mill or the like, depending upon the agglomerated state of the powder particles.

[3] Cosmetic Composition Containing Silicone Gel Cosmetic Powder

The silicone gel cosmetic powders according to the present invention can be used in a variety of cosmetic compositions, and for example, the powders are used for skin care products, skin care products, hair products, antiperspirant products, UV control products and the like, and particularly favorably are used in cosmetic compositions externally used for skins and hair. The mixing rate of the composite particles is not particularly limited, and they are appropriately selected in a range of 0.1 to 100.0 mass % relative to the entire cosmetic composition, depending upon the respective cosmetic compositions. Various components to be used in ordinary cosmetic compositions can be incorporated into the cosmetic compositions in such an amount that the effects of the present invention are not deteriorated. As such components, for example, an oily agent, a powder, a surface active agent, a water-soluble or water-swellable macromolecular compound, a UV absorbing agent, a moisturizing agent, an oil soluble gelatinizing agent, an antibacterial and antiseptic agent, salts, an antioxidant, an beauty skin ingredient (a beauty skin agent, a cell stimulant, a skin roughness improver, a blood circulation promoter, a skin astringent, an antiseborrheic agent, etc.), vitamins, amino acids, a antiperspirant, alcohols, a skin film forming agent, an anti-inflammatory agent, a refreshing agent, nucleic acids, hormones, a clathrate compound, a pH control agent, a chelate agent and other additives may be incorporated. They can be used singly or two or more kinds of them can be used in appropriately combined manners.

As the oily agent to be mixed into the cosmetic composition according to the present invention, any of a solid, a semi-solid and a liquid may be used. For example, natural animal and plant fats and oils and semi-synthesized fats and oils, a hydrocarbon oil, a higher alcohol, an ester oil, a silicone oil and a fluorine-type oil can be used.

Specifically, as the natural animal and plant fats and oils and semi-synthesized fats and oils, recitation is made of avocado oil, flaxseed oil, almonds oil, privet row, perilla oil, olive oil, cacao butter, kapok wax, Kaya oil, carnauba wax, cod-liver oil, candelilla wax, refined candelilla wax, beef fat and neat-foot oils, beef bone fat, hardened beef fat, apricot kernel oil, whale wax, hardened oil, wheat germ oil, sesame oil, rice germ oil, rice bran oil, sugarcane wax, camellia oil, safflower oil, shea butter, Paulownia mikado oil, cinnamon oil, Jojoba wax, squalane, squalene, shellac wax, turtle oil, soybean oil, tea seed oil, camellia oil, evening primrose oil, corn oil, prepared lard, rapeseed oil, Japanese paulownia oil, rice bran wax, germ oils, horse fat, persic oil, palm oil, palm kernel oil, castor oil, hydrogenerated castor oil, castor oil fatty acid methyl ester, sunflower seed oil, grape oil, bayberry wax, Jojoba oil, macadamia nut oil, yellow beeswax, mink oil, meadowfoam oil, cotton oil, cotton wax, Japanese kernel wax, Japanese wax kernel oil, montan wax, palm oil, hardened palm oil, glyceryl tricocoate, mutton tallow, peanut oil, lanolin, liquid lanolin, reduced lanolin, lanolin alcohol, hard lanolin, lanolin acetate, lanolin acetate alcohol, isopropyl lanolin fatty acid ester, polyoxyethylene lanolin alcohol ether, polyoxyethylene lanolin alcohol acetate, polyethylene glycol lanoline fatty acid ester, polyoxyethylene hydrogenated lanolin alcohol ether, yolk oil and the like.

As the hydrocarbon oils, straight-chain or branched and volatile hydrocarbon oils and the like are recited. For example, recitation is made of ozokerite, α-olefin oligomer, light isoparaffin, isododecane, isohexadodecane, light liquid paraffin, squalane, synthesized squalane, vegetable squalane, squalene, ceresin, paraffin, paraffin wax, polyethylene wax, polyethylene-polypropylene wax, (ethylene/propylene/styrene)copolymer, (butylene/propylene/styrene) copolymer, liquid paraffin, liquid isoparaffin, pristane, polyisobutylene, hydrogenated polyisobutene, microcrystalline wax, vaseline etc. As the higher fatty acid, recitation is made of lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, 12-hydroxystearic acid, etc.

As the higher alcohol, recitation is made of lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecynol, cholesterol, phytosterol, polyoxyethylene cholesterol ether, monostearyl glycerin ether (batyl alcohol), monooleylglyceryl ether (celachyl alcohol) and the like.

As the ester oils, di-isobutyl adipate, 2-hexyldecyl adipate, di-2-heptylundecyl adipate, N-alkyl glycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerithritol tetra-2-ethylhexanoate, cetyl octanoate, octyldodecyl gum ester, oleyl oleate, octyldocecyl oleate, decyl oleate, neopentyl glycol dioctanoate, neopentyl glycol dicaproate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyl octanoate, ethyl laurate, hexyl laurate, N-lauroyl-L-glutamic acid-2-octyldodecyl ester, lauroyl sarcosine isopropyl ester, diisostearyl malate and the like; glyceride oils such as acetoglyceryl, glyceryl triisooctanoate, glyceryl triisostearate, glyceryl triisopalmitate, glyceryl tribehenate, glyceryl monostearate, glyceryl di-2-heptylundecanoate, glyceryl trimyristate, diglyceryl myristate isostearate, etc.

As the silicone oils, recitation is made of straight-chain or branched organopolysiloxane having a low viscosity to a high viscosity, such as dimethylpolysiloxane, tristrimethylsiloxymethyl silane, caprylyl methicone, phenyl trimethicone, tetrakistrimethylsiloxysilane, methyl phenylpolysiloxane, methylhexylpolysiloxane, methyl hydrogen polysiloxane, dimethylsiloxane-methylphenyl siloxane copolymer, etc.; cyclic organopolysiloxanes such as Octamethyl cyclotetrasiloxane, decamethylcyclopentasiloxane, dodecamethylcyclohexasiloxane, tetramethyl tetrahydrogen cyclotetrasiloxane, tetramethyl tetraphenyl cyclotetrasiloxane, etc.; amino-modified organopolysiloxane, pyrrolidone-modified organopolysiloxane, pyrrolidone carboxylic acid-modified organopolysiloxane, silicone rubbers such as gum-like dimethyl polysiloxane having a high polymerization degree, gum amino-modified organopolysiloxane, gum imethylsiloxane-methylphenylsiloxane copolymer, silicone gum and cyclic organopolysiloxane gum solution; trimethylsiloxy silicate, cyclosiloxane solution of trimethylsiloxy silicate, higher alkoxy-modified silicones such as stearoxy-silicone, higher fatty acid-modified silicones, alkyl-modified silicone, long-chain alkyl-modified silicone, amino acid-modified silicone, fluorine-modified silicone, silicone resin, melt of silicone resin, etc.

As fluorine-series oils, perfluoropolyethers, perfluorodecalin, perfluorooctane and the like are recited. The mixing amount of the oil is appropriately selected in a range of 1 to 90 mass % relative to the entirety of the cosmetic composition depending upon formulations.

As the powder, inorganic particles, organic particles, inorganic-organic composite powders, silicone resin particles, etc. are recited. As the inorganic particles, the resin particles, the inorganic-organic composite powders, silicone resin particles, the same inorganic particles, the same resin particles and the same inorganic-organic composite powders as mentioned above to be used in the present invention are recited, by way of examples. As the silicone resin particles, particles such as silicone elastomeric particles, polymethylsilsesquioxane particles, and silicone elastomeric particles surface-coated with polymethylsilsesquioxane, etc. are recited. As to these powders, use can be made of ones having surfaces treated with a silylating agent, a silicone oil, a silicone resin, waxes, paraffins, an organofluorine compound, acylated amino acids, lecithin, an ester oil and the like are recited.

As the surface active agents, non-ionic, anionic, cationic and amphoteric activators are recited, and the same ones as used in the production of the composite particles according to the present invention. Among these surface active agents, a straight-chain or branched polyoxyethylene-modified organopolysiloxane, a straight-chain or branched polyoxyethylenepolyoxypropylene-modified organopolysiloxane, a straight-chain or branched polyoxyethylene-alkyl co-modified organopolysiloxane, a straight-chain or branched polyoxyethylene-polyoxypropylene-alkyl co-modified organopolysiloxane, a straight-chain or branched polyglycerin-modified organopolysiloxane, and a straight-chain or branched polyglycerin-alkyl co-modified organopolysiloxane are preferable. In these surface active agents, the content of hydrophilic polyoxyethylene groups, polyoxyethylene-polyoxypropylene groups or polyglycerin residue preferably amounts to 10 to 70 mass % relative to the molecule. The mixing amount is preferably 0.1 to 20 mass %, more preferably 0.2 to 10 mass % relative to the entirety of the cosmetic composition. The HLB of the surface active agent is not limited, but preferably 2 to 14.5.

As the water-soluble or water-swellable macromolecular compounds, recitation is made of plant-based polymers such as gum arabic, tragacanth, galactan, carob gum, guar gum, karaya gum, carrageenan, pectin, agar, quince seed (quince), starch (rice, corn, potato, wheat), dextrin, dextoran, argecolloid, trant gum, locust bean gum, etc.; microorganism-based water-soluble polymers such as xanthane gum, dextran, succinoglucan, pullulan, etc.; animal-based water-soluble macromolecular compounds such as collagen, casein, albumin, gelatin, etc.; starch-based polymers such as carboxymethyl starch, methylhydroxypropyl starch, etc.; cellulose-based macromolecular compounds such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose and cellulose powder; alginic acid-based macromolecular compounds such as sodium alginate, alginic acid propylene glycol ester, etc.; vinyl-based macromolecular compounds such as polyvinylmethyl ether, carboxyvinyl polymer, etc.; polyoxyethylene-based macromolecular compounds, polyoxyethylene polyoxypropylene copolymer-based macromolecular compounds, acryl-based water soluble macromolecular compounds such as sodium polyacrylate, polyethyl acrylate, polyacrylamide, acryloyldimethyl taurin salt copolymer, etc.; other synthetic macromolecular compounds such as polyethylene imine, cation polymer, etc.; and inorganic water-soluble macromolecular compounds such as bentonite, magnesium aluminum silicate, montmorillonite, beidellite, nontronite, saponite, hectorite, silicic anhydride, etc. In addition, these water-soluble macromolecular compounds include film-forming agents such as polyvinyl alcohol, polyvinyl pyrolidone, etc. The mixing amount is preferably in a range of 0.1 to 25 mass % relative to the entirety of the cosmetic composition.

As the UV absorbing agents, recitation is made of benzoic acid-based UV absorbing agents such as paraaminobenzoic acid, etc.; anthranilic acid-based UV absorbing agents such as methyl anthranilate, etc.; salicylic acid-based UV absorbing agents such as methyl salicylate, octyl salicylate, and trimethylcyclohexyl salicylate, etc.; cinnamic acid-based UV absorbing agents such as octyl para methoxy cinnamate; benzophenone-based UV absorbing agents such as 2,4-dihydroxybenzophenon, etc.; urocanic acid-based UV absorbing agents such as ethyl urocanate, etc.; dibenzoyl methane-based UV absorbing agents such as 4-t-butyl-4'-methoxy-dibenzoyl methane, etc.; and phenylbenzoyl imidazole sulfonic acid, triazine derivatives, etc. As the UV absorption dispersing agents, finely particular titanium oxide, finely particular iron-containing titanium oxide, finely particular zinc oxide, finely particular cerium oxide, finely particular iron oxide and composite bodies thereof, and particles capable of absorbing and dispersing ultraviolet rays. Dispersions in which these particles capable of absorbing and dispersing ultraviolet rays are preliminarily dispersed can be used.

As the moisturizing agents, mention may be made of glycerin, sorbitol, propylene glycol, dipropylene glycol, 1,3-butylene glycol, pentylene glycol, glucose, xylitol, maltitol, polyethylene glycol, hyaluronic acid, chondroitin sulfate, pyrolidone carboxylic acid salt, polyoxyethylene methyl glucoside, polyoxypropylene methyl glucoside, yolk lecithin, soy lecithin, phosphatidylcholine, phosphatidylethanolamine, phosphatidyl serine, phosphatidyl glycerol, phosphatidylinositol, sphingo phospholipid and the like.

As the oil-soluble gelatinizing agents, metal soaps such as aluminum stearate, magnesium stearate, zinc myristate and the like; amino acid derivatives such as N-laurolyl-L-glutamic acid dibutyl amide, N-2-ethylhexanoly-L-glutamic acid dibutyl amide and the like, dextrin fatty acid esters such as dextrin palmitin acid ester, dextrin stearic acid ester, dextrin 2-ethyl hexanoic acid palmitin acid ester and the like; saccharose fatty acid esters such as saccharose palmitin acid ester, saccharose stearic acid esters and the like; fructo-oligosaccharide stearic acid esters such as fructo-oligosaccharide stearic acid ester, fructo-oligosaccharide 2-ethyl hexanoic acid ester and the like; sorbitol benzylidene derivatives s such as monobenzylidene sorbitol, dibenzylidene sorbitol and the like; organic modified clay minerals such as dimethylbenzyldodecyl ammonium montmorilonite clay, dimethyldioctadecyl ammonium montmorilonite clay and the like.

As the antimicrobial preservative and antiseptic agents, recitation is made of a para-oxybenzoic acid alkyl ester, benzoic acid, sodium benzoate, sorbic acid, a potassium sorbate, phenoxy ethanol, etc. As the antibacterial agents, benzoic acid, salicylic acid, carbolic acid, sorbic acid, paraoxybenzoic acid alkyl esters, parachrol metacresole, hexachlorophene, benzalkonium chloride, chlorhexidine chloride, trichlorocarbanilide, photosensitizer, phenoxyethanol and the like.

As salts, inorganic salts, organic acid salts, amine salts, and amino-acid salts are recited. As the inorganic salts, for instance, sodium salts, potassium salts, magnesium salts, calcium salts, aluminum salts, zirconium salts, and zinc salts, etc. of inorganic acids such as hydrochloric acid, sulfuric acid, carbonic acid, nitric acid, etc. can be recited. As the organic acid salts, for instance, recitation is made of salts of organic acids such as acetic acid, dehydroacetic acid, citric acid, malic acid, succinic acid, ascorbic acids, stearic acid and the like; as the amine salt and the amino-acid salt, for instance, salts of amines such as triethanolamines, salts etc. of amino acids such as glutamic acids, etc. Moreover, additionally, use may be made of salts of hyaluronic acid, chondroitin sulfate, etc., aluminum zirconium glycine complex, and further a neutralized salt of as an acid-an alkali to be used in cosmetic preparations.

As to the antioxidants, tocopherol, p-t-butylphenol, butylhydroxyanisole, dibutylhydroxytoluene, phytic acid, etc. may be recited. As to the pH regulator, lactic acid, citric acid, glycolic acid, succinic acid, tartaric acid, dl-malic acid, potassium carbonate, sodium hydrogen carbonate, ammonium hydrogen carbonate, etc. may be recited. As a chelating agent, alanine, sodium edatate, sodium polyphosphate, sodium metaphosphate, phosphoric acid, etc, may be recited. As to a freshner, L-menthol, camphor, etc. may be recited. As an anti-inflammatory agent, allantoin, glycyrrhizic acid and salts thereof, glycyrrhizic acid, and stearyl glycyrrhizinate, tranexamic acid, azulene, etc. may be recited.

As an element for beautiful skin, whitening agents such as placenta extracted liquids, arbutin, glutathione, saxifrage extracted material, etc.; hepatocyte activators such as royal jelly, photosensitizer, cholesterol derivatives, infant cow blood extracted liquid, etc.; kin roughness improving agent; blood flow enhancing agent, 4-hydroxy-3-methoxybenzyl nonylic acid amide, benzyl nicotinate, β-butoxethyl nicotinate, capsaicin, zingerone, cantharides tincture, ichthammol, caffeine, tannic acid, α-borneol, tocopherol nicotinate, inositol hexanicotinate, cyclandelate, cinnarizine, tolazoline, acetylcholine, verapamil, cepharanthine, γ-oryzanol, etc.; skin astringents such as zinc oxide, tannic acid etc., antiseborrheic agents such as sulfur, thiane troll, etc., may be recited.

As the vitamin group, vitamin A such as vitamin A oil, retinol, retinol acetate, retinol palmitate, etc.; vitamin B including vitamin B2 such as riboflavin, riboflavin tetrabutyrate, flavin adenine nucleotide, etc.; vitamin B6 such as pyridoxine hydrochloride, pyridoxine dioctanoate, pyridoxine tripalmitate, etc.; vitamin B12 and its derivatives, vitamin B15 and its derivatives; vitamin C including L-ascorbic acid, L-ascorbic acid/dipalmitin acid ester, L-ascorbic acid-2-sodium sulfate, L-ascorbic acid phosphoric acid diester dipotassium, etc.; vitamin D such as ergocalciferol, cholecalciferol etc.; vitamin E such as α-tocopherol, β-tocopherol, γ-tocopherol, acetic acid dl-α-tocopherol, nicotinic acid group such as nicotinic acid dl-α-tocopherol, succinic acid dl-α-tocopherol etc.; vitamin E; nicotinic acid, benzyl nicotinate, nicotinamide etc.; vitamin H, vitamin P, pantothenic acid derivatives such as calcium pantothenate, D-pantothenyl alcohol, pantothenyl ethyl alcohol, acetyl pantothenyl ethyl, etc., biotin etc. are recited.

As amino acids, recitation is made of glycine, valine, leucine, isoleucine, serine, threonine, phenylalanine, arginine, lysine, aspartic acid, glutamic acid, cystine, cysteine, methionine, tryptophane, etc. As a nucleic acid, deoxyribonucleic acid etc. are recited. As a hormone, estradiol, ethenyl estradiol, etc. may be recited.

As an antiperspirant, aluminum chlorohydrate, aluminum chloride, aluminum sesquichlorohydrate, zirconyl hydroxychloride, aluminum zirconium hydroxychloride, aluminum zirconium glycine complex etc.

The cosmetic compositions of this invention may be in the form of powders, oils, multi-emulsions such as water-in oil emulsions, oil-in water emulsions, non-aqueous emulsions, W/O/W or O/W/O, etc. Moreover, the cosmetic compositions of this invention may be in a state of a liquid, a milky lotion, a cream, a solid, a paste, a gel, a powder, a pressed matter, a multi-layer, a mousse, a spray, a stick, a pencil or the like. In addition, as examples of the cosmetic compositions, recitation is made of skin care cosmetic compositions such as skin lotion, milky lotion, cream, cleansing, packing, oil liquid, massage materials, beauty liquid, beauty oil, cleaning agent, deodorizer, hand cream, lip cream, anti-wrinkle products, etc.; makeup cosmetic compositions such as makeup base, concealer, white powder, powder foundation, facial liquid foundation, cream foundation, oily foundation, rouge, eye shadow, mascara, eyeliner, eyebrow, lipstick, etc.; hair cosmetic compositions such as shampoo, rinse, treatment, and hair styling agent, etc.; antiperspirant, ultraviolet rays defense makeup cosmetic compositions such as sunscreen oil, sunscreen milky lotion, sunscreen cream, etc.

Moreover, these cosmetic compositions may be in various forms including a state of a liquid, a milky lotion, a cream, a solid, a paste, a gel, a powder, a pressed matter, a multi-layer, a mousse, a spray, a stick, a pencil, etc.

EXAMPLES

In the following, the present invention will be explained by showing examples and comparative examples, but the invention is not limited to the following examples.

A dimethiconol oil (α,ω-dihydroxypolydimethylsiloxane having a viscosity of 30 mPa·s) was prepared as a diorganopolysiloxane having reactive opposite ends. A water emulsion of dimethiconol was prepared by the following method.

Production Example 1 for a Water Emulsion of Dimethiconol by Mechanical Emulsification Dimethiconol having the above viscosity of 30 mPa·s, 500 g, was charged into a polyethylene beaker with a volume of 2 liters, and 22.5 g of sodium lauroylmethyl taurate and 50 g of ion-exchanged water were gradually dropped thereto under stirring with a homomixer at 5,000 rpm, thereby effecting phase inversion. After increasing the viscosity, the stirring speed was increased to 7,000 rpm, then stirred for 15 minutes, and the mixture was diluted with the addition of 450 g of ion-exchanged water. Thereafter, the resultant was emulsified and dispersed once in a portable press homogenizer (manufactured by APV Gaulin) at 70 MPa, thereby obtaining an emulsion. A solid component was obtained by evaporating off water by drying the water emulsion at 105°

C. for 3 hours. its molecular weight was determined to be 6,000 as PS conversion by GPC. The solid component was 51.0%.

Production Example 2 for a Water Emulsion of Dimethiconol by Emulsion Polymerization Dimethiconol having the above viscosity of 30 mPa·s, 500 g, was charged into a polyethylene beaker with a volume of 2 liters, 22.5 g of sodium lauroylmethyl taurate and 50 g of ion-exchanged water were gradually dropped thereto under stirring with a homomixer at 5,000 rpm, thereby effecting phase inversion. After increasing the viscosity, the stirring speed was increased to 7,000 rpm, and then stirred for 15 minutes, and the mixture was diluted with the addition of 450 g of ion-exchanged water. Thereafter, the resultant was emulsified and dispersed once in a portable press homogenizer (manufactured by APV Gaulin) at 70 MPa. After 4.5 g of citric acid as a condensation polymerization catalyst was added thereto and stirred, the mixture was subjected to a condensation polymerization reaction for 10 hours. Thereafter, the resultant was adjusted to pH7 by adding 10% sodium carbonate, thereby obtaining a water emulsion, and a solid component was obtained by evaporating off water by drying the water emulsion at 105° C. for 3 hours. its molecular weight was determined to be 150,000 as PS conversion by GPC. The solid component was 49.5%.

Production Example 3 for a Water Emulsion of Dimethiconol by Emulsion Polymerization Octamethylcyclotetrasiloxane, 450 g, 500 g of ion-exchanged water and 6.7 g of sodium lauroylmethyl taurate and were charged into a polyethylene beaker with a volume of 2 liters, and the mixture was preliminarily stirred with a homomixer at 2,000 rpm. Thereafter, 4 g of citric acid was added to the resultant, which was heated to 70° C., and subjected to emulsion polymerization at 5,000 rpm in a homomixer for 24 hours. A water emulsion of dimethiconol having a high molecular weight was obtained by emulsifying and dispersing the resultant by the portable press homogenizer (manufactured by APV Gaulin) once at 50 MPa. Thereafter, the resultant was adjusted to pH7 by adding 10% sodium carbonate, thereby obtaining a water emulsion. A solid component was obtained by evaporating off water by drying the water emulsion at 105° C. for 3 hours, and its molecular weight was determined to be 10,000 as PS conversion by GPC. The solid component was 46.5%.

The following compounds were prepared as crosslinking agents of dimethiconol. 1. Product name: KBE-903 (aminopropyltriethoxysilane: Shin-Etsu Chemical Co., Ltd.), 2. Product name: KBE-13 (methyltriethoxysilane: Shin-Etsu Chemical Co., Ltd.), 3. Product name: KF-9901 (methyl hydrogen polysiloxane (the number of Si—O units being about 40, Si-2CH3/Si—CH3H ratio=1/1:Shin-Etsu Chemical Co., Ltd.). Finely crosslinked reaction products of silicone were obtained with mixtures shown in Table 1, and mixing ratios at which silicone gels were obtained were confirmed. A method for preparing the reaction product of silicone was shown below.

(Preparation of a Finely Crosslinked Reaction Product of Silicone)

In a 300 ml vessel made of PP, 0.1 g of sodium lauroylmethyl taurate was dissolved into 100 g of ion-exchanged water, 10 g of diorganopolysiloxane oil (A) with reactive opposite ends was gradually added thereto in a homomixer under stirring at 6000 rpm. The resultant was maintained stirred for 10 minutes and emulsified at a room temperature, thereby obtaining a water emulsion. Into this emulsion was added the crosslinking agent (B) 25 wt % IPA solution under stirring by a stirrer. Then, if necessary, the resultant was adjusted to pH10.5 with a 1N—NaOH aqueous solution, which was stirred for 15 minutes and moved in an aluminum plate. A silicone reaction product was obtained by evaporating water at 105° C./24 h. In case that the diorganopolysiloxane with the reactive opposite ends is a water emulsion, the water emulsion having 10 g of a solid component was charged, and subjected to the same steps as mentioned above with the ion-exchanged water such that the content of the water is 100 g. The mixing weight ratio (A)/(B) between the diorganopolysiloxane with the reactive opposite ends (A) and the crosslinking agent (B) was set at either 100/10, 7/1 or 3/1.

(Measuring Condition with a Durometer AO)

A silicone reaction product was charged into a styrol square case (vertical 36 mm×lateral 36 mm×height 14 mm) such that it protruded slightly from a face of the case, and the surface of the reaction product was flattened as a test surface. A press plate of a durometer was set over the test surface by 20 mm, and a scale of a needle was read by pressing the press plate onto the test piece in the state that the surface of the test face and the press plate were being maintained in parallel. This operation was carried out 5 times, and a measured value was obtained by the averaged value. Note that when the needle was not moved in the measurement, it was called NA (Not Applicable).

(Measuring Condition of a Complex Modulus and Tan δ in a Dynamic Viscoelasticity Measurement)

Under conditions shown below, G' (storage modulus) and G" (loss modulus) were determined, and a complex modulus and tan δ were determined.

[Formula 1]

$$\text{Complex modulus} = \sqrt{G'^2 + G''^2} \quad (1)$$

$$\tan \delta = G''/G' \quad (2)$$

Viscoelasticity measuring device: Rheosol-G3000 (manufactured by UBM)
Measuring jig: Parallel plate in 20 mm diameter
Measuring frequency: 4 Hz
Measuring temperature: 25±1.0° C.
Setting of distortion in measurement: A distortion rate was set at 17%, and measurement was effected in an automatic measuring mode.
Thickness (gap) of a sample to be measured: 1.0 mm

TABLE 1

| Comp. No. | Dimechikonol (A) | Crosslinking agent (B) | (A)/(B) wt % ratio | Duometer AO Value | Complex modulus | tan δ |
|---|---|---|---|---|---|---|
| 1 | Viscosity 30 mPa · s | KBE-903 | 100/10 | N/A | 23.217 | 1.051 |
| 2 | Viscosity 30 mPa · s | KF9901 | 3/1 | N/A | 11.267 | 1.668 |
| 3 | Water emulsion in Producing Example 1 | KBE-903 | 100/10 | N/A | 39.503 | 1.187 |

TABLE 1-continued

| Comp. No. | Dimechikonol (A) | Crosslinking agent (B) | (A)/(B) wt % ratio | Duometer AO Value | Complex modulus | tan δ |
|---|---|---|---|---|---|---|
| 4 | Water emulsion in Producing Example 1 | KF-9901 | 3/1 | N/A | 37.622 | 1.268 |
| 5 | Water emulsion in Producing Example 1 | KF-9901 | 7/1 | N/A | 14.399 | 1.486 |
| 6 | Water emulsion in Producing Example 1 | KBE-13 | 3/1 | N/A | 217.564 | 0.812 |
| 7 | Water emulsion in Producing Example 1 | KBE-13 | 7/1 | N/A | 77.368 | 1.578 |
| 8 | Water emulsion in Producing Example 3 | KF-9901 | 3/1 | N/A | 13.187 | 1.942 |
| 9 | Water emulsion in Producing Example 2 | KF-9901 | 7/1 | N/A | 9.351 | 2.376 |
| 10 | Water emulsion in Producing Example 2 | KBE-13 | 3/1 | N/A | 72.675 | 1.416 |
| 11 | Water emulsion in Producing Example 2 | KBE-13 | 7/1 | N/A | 69.744 | 1.799 |
| 12 | Water emulsion in Producing Example 3 | KBE-903 | 100/10 | N/A | 17.464 | 1.353 |
| 13 | Water emulsion in Producing Example 3 | KF-9901 | 3/1 | N/A | 10.1808 | 1.934 |
| 14 | Water emulsion in Producing Example 3 | KF-9901 | 7/1 | N/A | 5.968 | 1.901 |
| 15 | Water emulsion in Producing Example 3 | KBE-13 | 3/1 | N/A | 72.069 | 1.182 |
| 16 | Water emulsion in Producing Example 3 | KBE-13 | 7/1 | N/A | 35.882 | 1.674 |

The compositions other than Composition No. 6 exhibited properties of preferred silicone gels according to the present invention.

[Production of Cosmetic Powders Surface-Treated with Silicone Gels]

Example 1

Ration of Dimethiconol/Crosslinking Agent=100/10 wt %

Talc JA-13R (manufactured by Asada Seifun Co., Ltd.), 1 kg, was charged into a universal mixer, 550 g of water and a mixed liquid of IPA/dimethiconol having a viscosity of 30 mPa·s=60 g/35 g were mixed thereinto. The resultant was mixed under stirring for 15 minutes, thereby obtaining a soft paste (in a capillary state) of the powder particles. A 5 mass % KBE-903 aqueous solution, 70 g, was added thereto as a crosslinking agent, further followed by mixing and stirring for 15 minutes. After the soft paste was taken out, it was dried at 120° C. for 16 hours in a dryer. At that time, when an internal temperature was recorded in a state that a temperature sensor was inserted into the past, it was revealed that the paste was heated at the internal temperature of 115° C. or more for 5 hours. Talc surface-treated with silicone gel at 3% was obtained by pulverizing the dried cake with a pulverizer.

Example 2

Ratio of Dimethiconol/Crosslinking Agent=100/10 wt %

Into a PE-made vessel with a volume of 20 liters were charged 7 L of water and 1 kg of sericite FSE (manufactured by Sanshin Mine Industrial Co., Ltd.), which was dispersed (in a slurry state) at 2000 rpm for 5 minutes in a disperser mixer (Prime Mix Co., Ltd.; AM-40). Then, 103 g of the water emulsion of dimethiconol (Producing Example 3) was added thereinto, which was stirred at 2500 rpm for 5 minutes. Thereafter, 96 g of a 5 wt % aqueous solution of KBE-903 was added as a crosslinking agent. After the resultant was adjusted to pH10.3 with a 1N—NaOH aqueous solution, the resultant was reacted under stirring at 3000 rpm for 30 minutes. After the resultant was filtered with a centrifugal dewatering machine and washed with 7 L of water, the dewatered cake was dried at 120° C. for 16 hours in a dryer. At that time, when an internal temperature was recorded in a state that a temperature sensor was inserted into the cake, it was revealed that the cake was heated at the internal temperature of 115° C. or more for 7 hours. Sericite surface-treated with silicone gel at 5% was obtained by pulverizing the dried cake with the pulverizer.

Example 3

Ratio of Dimethiconol/Crosslinking Agent=4/1 wt %

A synthesized mica PDM-9WB (manufactured by Topy Industries Ltd.), 1 kg, was charged into the universal mixer, and a water emulsion of 450 g of water and 82.6 g of dimethiconol (Producing Example 1) was added thereinto, and a soft paste (in a capillary state) was obtained by stirring for 15 minutes. KF-9901, 10.5 g, was added as a crosslinking agent to the resultant, and 4 ml of a 28% ammonia aqueous solution was added thereto, followed by mixing and stirring for 15 minutes. The resultant was taken out, and was dried at 140° C. for 16 hours in a dryer. At that time, when an internal temperature was recorded in a state that a temperature sensor was inserted into the paste, it was revealed that the paste was heated at the internal temperature of 135° C. or more for 8 hours. A synthetic mica surface-treated with silicone gel at 5% was obtained by pulverizing the dried cake with the pulverizer.

Example 4

Ratio of Dimethiconol/Crosslinking Agent=100/10 wt %

Water, 7 L, and a 1N—NaOH aqueous solution were charged into a PE-made vessel with a volume 20 liters to adjust the pH to 12.0. After 1 kg of titanium oxide CR-50 (manufactured by Ishihara Sangyo Kaisha, Ltd.) was added to the resultant, followed by dispersing (in a slurry state) at 3000 rpm for 5 minutes in a disperser mixer (Prime Mix Co., Ltd.; AM-40). Then, 96 g of a 5 wt % aqueous solution of KBE-903 was added as a crosslinking agent, followed by stirring at 2000 rpm for 5 minutes. Thereafter, 97 g of the water emulsion of dimethiconol (Producing example 2) was added to the resultant, which was stirred at 3000 rpm for 30 minutes, while kept at pH10.3 or more. After the resultant was filtered with the centrifugal dewatering device and washed with 7 L of water, and the dewatered cake was dried at 120° C. for 16 hours in the dryer. At that time, when an internal temperature was recorded in a state that a temperature sensor was inserted into the past, it was revealed that the mixture was heated at the internal temperature of 115° C. or more for 5 hours. The titanium oxide surface-treated with silicone gel at 5% was obtained by pulverizing the dried cake with the pulverizer.

Example 5

Ratio of Dimethiconol/Crosslinking Agent=100/10 wt %

Water, 5 L, and a 1N—NaOH aqueous solution were charged into a PE-made vessel with a volume 20 liters to adjust the pH to 12.0. After 700 g of talc FK300S (manufactured by Yamaguchi Unmo Industries, Ltd.) was added to the resultant, followed by dispersing (in a slurry state) at 3000 rpm for 5 minutes in the disperser mixer (Prime Mix Co., Ltd.; AM-40). (Talc slurry) Water, 3 L, and 300 g of finely particulate titanium oxide TTO-55A (manufactured by Ishihara Sangyo Kaisha, Ltd.) were charged into another vessel, the resultant was adjusted to pH12.0 with a 1N—NaOH aqueous solution, and the resultant was dispersed at 6,000 rpm for 10 minutes with the homomixer. (Slurry of finely particulate titanium oxide) After the talc slurry was gradually added to a slurry of finely particulate titanium oxide under stirring at 3000 rpm with the disperser mixer, 116 g of the 5 wt % aqueous solution of KBE-903 was added as a crosslinking agent to the mixture, followed by stirring at 3000 rpm for 5 minutes. Further, 117 g of the water emulsion of dimethiconol (Producing example 2) was added to the resultant, which was stirred at 3000 rpm for 30 minutes, while the pH was keep at 10.3 or more. After the resultant was filtered with the centrifugal dewatering device and the resultant was washed with 8 L of water, the dewatered cake was dried at 120° C. for 16 hours in the dryer. At that time, when an internal temperature was recorded in a state that a temperature sensor was inserted into the cake, it was revealed that the cake was heated at the internal temperature of 115° C. or more for 5 hours. The finely particulate titanium oxide-coated talk surface-treated with silicone gel at 6% was obtained by pulverizing the dried cake with the pulverizer.

Example 6

Ratio of Dimethiconol/Crosslinking Agent=100/10 wt %

Timiron Super Red surface-treated with silicone gel at 5% was obtained in the same manner except that the sericite in Example 2 was replaced by Timiron Super Red (manufactured by Merck Co., Ltd.)

Example 7

Ratio of Dimethiconol/Crosslinking Agent=100/10 wt %

Yellow LL-100P surface-treated with silicone gel at 5% was obtained in the same manner except that the titanium oxide in Example 4 was replaced by Yellow iron oxide: Yellow LL-100P (manufactured by Titan Kogyo, Ltd.)

Example 8

Ratio of Dimethiconol/Crosslinking Agent=100/10 wt %

Red R-516PS surface-treated with silicone gel at 5% was obtained in the same manner except that the titanium oxide in Example 4 was replaced by yellow iron oxide: Red R-516PS (manufactured by Titan Kogyo, Ltd.).

Example 9

Ratio of Dimethiconol/Crosslinking Agent=100/10 wt %

Black BL-100P surface-treated with silicone gel at 5% was obtained in the same manner except that the titanium oxide in Example 4 was replaced by yellow iron oxide: Black BL-100P (manufactured by Titan Kogyo, Ltd.).

Example 10

Ratio of Dimethiconol/Crosslinking Agent=100/10 wt %

Methyl polymethacrylate surface-treated with silicone gel at 3% was obtained in the same manner except that the talc in Example 1 was replaced by crosslinkable spherical methyl polymethacrylate (Product Name: Gantsu Pearl GMX-0810, manufactured by Gantsu Kasei, Ltd.).

Example 11

Ratio of Dimethiconol/Crosslinking Agent=7/1 wt %

Water, 7 L, and a 1N—NaOH aqueous solution were charged into a PE-made vessel with a volume of 20 liters to adjust the pH to 12.5. Then, 1 kg of finely particulate titanium oxide TTO-S-3 (manufactured by Ishihara Sangyo Kaisha, Ltd.) was added to the resultant, which was dispersed at 3000 rpm for 5 minutes (in a slurry state) in the disperser mixer (Prime Mix Co., Ltd.; AM-40). Then, 21 g of a water emulsion of KF-9901 (silicone/sodium lauroyl-methyl taurinate/water=45/5/50 wt % was added to the resultant as a crosslinking agent, which was stirred at 3000 rpm for 5 minutes. Furthermore, 133 g of the water emulsion of dimethiconol (Producing example 2) was added to the resultant, which was stirred at 3000 rpm for 60 minutes, while the pH was kept at 10.5 or more. After the resultant was filtered with the centrifugal dewatering device and the resultant was washed with 7 L of water, the dewatered cake was dried at 120° C. for 16 hours in the dryer. At that time, when an internal temperature was recorded in a state that a temperature sensor was inserted into the cake, it was revealed that the cake was heated at the internal temperature of 115° C. or more for 6 hours. The finely particulate titanium oxide surface-treated with silicone gel at 7% was obtained by pulverizing the dried cake with a JET mill.

Comparative Examples 1 to 11

Powders Surface-Treated with the Silicone Gel of the Above Composition No. 6

Respective surface-treated powders surface-treated were obtained in the same producing methods and in the same surface treatments as in the respective Examples except that the surface treating agents used in Examples 1 to 11 were replaced by the water emulsion of dimethiconol in Producing example 1 and KBE-13.

(Evaluation of Water Repellency)

Water, 60 ml was placed in a 100 ml beaker, into which 0.5 g of each of the surface-treated powders was fed and kept still for 24 hours. Then, after the resultant was stirred 50 times by a spatula at a speed of 2 times per second, a transfer state of the surface-treated powder into an aqueous phase was evaluated as shown below.

TABLE 1-2

◎: The powder was kept floated on the surface of the water, and not transferred into the aqueous phase.
○: While the powder was kept floated, the aqueous phase was slightly cloudy.
Δ: While the powder was kept floated, the aqueous phase was cloudy.
X: While a part of the powder was kept floated, the aqueous phase was largely cloudy.

(Evaluation of Usability)

Each of the samples was coated on a brachial region in an amount of 0.3 mg/cm2, and light usability and moist feeling were evaluated based on smoothness observed when the coated region was rubbed with a foundation sponge three times. The evaluations were made into 5 stages with marks according to the following absolute evaluations by 10 persons of an expert evaluation panel. As to each of the samples, the average value was calculated from the total marks of all the persons of the panel, and judgment was made according to the following four stages.

(Absolute Evaluation)
(Marks)
  Evaluations
  5: Very good
  4: Good
  3: Medium
  2: Slightly bad
  1: Bad

TABLE 2

(Judgment standard)

| Average value of marks | Judgment | |
|---|---|---|
| 4. 5 or more | Very good | ◎ |
| 3. not less than 4.5 and less than 5 | Good | ○ |
| 2. not less than 3.5 and less than 4.5 | Slightly bad | Δ |
| 1. less than 3.5 | Bad | X |

(Evaluation of Adhesion to Skin)

One sample was coated at two locations of a brachial region each in 0.3 mg/cm2. Water at 38° C. was flown on one location for 10 minutes, whereas no water was flown on the other location as a standard. Change in the coated film on the water-flown location was visually observed as compared with the standard. The evaluations were made into 5 stages with marks according to the following absolute evaluations by 10 persons of an expert evaluation panel. As to each of the samples, the average value was calculated from the total marks of all the persons of the panel, and judgment was made according to the following four stages.

(Absolute Evaluation)
(Marks)
  Evaluations
  5: Completely no change.
  4: A slightly thin film was formed, and a slight difference was observed.
  3: The coated film was thin, and a difference was observed.
  2: Although a considerable thin film was formed, powder remained.
  1: Almost no powder remained.

TABLE 3

(Judgment standard)

| Average value of marks | Judgment | |
|---|---|---|
| 4. 5 or more | Very good | ◎ |
| 3. not less than 4.5 and less than 5 | Good | ○ |
| 2. not less than 3.5 and less than 4.5 | Slightly bad | Δ |
| 1. less than 3.5 | Bad | X |

(Evaluation Results)

Evaluation results of the surface-treated powders in Examples and Comparative Examples were shown in Table 4.

TABLE 4

| | Water Repellency | Smoothness & lightness | Moist Feeling | Adhesion to skin |
|---|---|---|---|---|
| Example 1 | ◎ | ◎ | ◎ | ◎ |
| Example 2 | ◎ | ◎ | ◎ | ◎ |
| Example 3 | ◎ | ◎ | ◎ | ◎ |
| Example 4 | ◎ | ◎ | ◎ | ◎ |
| Example 5 | ◎ | ◎ | ◎ | ◎ |
| Example 6 | ◎ | ◎ | ◎ | ◎ |
| Example 7 | ◎ | ○ | ○ | ○ |
| Example 8 | ◎ | ○ | ○ | ○ |
| Example 9 | ◎ | ○ | ○ | ○ |
| Example 10 | ◎ | ○ | ○ | ○ |
| Example 11 | ◎ | ◎ | ◎ | ○ |
| Comp. Exam. 1 | ○ | Δ | ○ | Δ |
| Comp. Exam. 2 | X | Δ | ○ | Δ |
| Comp. Exam. 3 | X | Δ | ○ | Δ |
| Comp. Exam. 4 | X | X | X | Δ |
| Comp. Exam. 5 | Δ | Δ | Δ | Δ |
| Comp. Exam. 6 | X | Δ | ○ | Δ |
| Comp. Exam. 7 | ○ | X | X | Δ |

TABLE 4-continued

|  | Water Repellency | Smoothness & lightness | Moist Feeling | Adhesion to skin |
|---|---|---|---|---|
| Comp. Exam. 8 | ○ | X | X | Δ |
| Comp. Exam. 9 | ○ | Δ | Δ | Δ |
| Comp. Exam. 10 | ○ | Δ | ○ | X |
| Comp. Exam. 11 | X | X | X | X |

As is clear from Table 4, it is demonstrated that the cosmetic powders according to the present invention are more excellent in water repellency, smoothness and lightness, moist feeling and adhesion to skin, as compared with the powders in Comparative examples.

Next, evaluations were made of formulations of cosmetic compositions into which the surface-treated powders in Examples and Comparative Examples were mixed. As regards each of the formulations obtained, 50 female women of an expert panel evaluated smoothness and lightness, moist feeling, usability such as spreading, adhesion to skin, uniformity in makeup finish, and makeup durability according to evaluation standards shown in Table 5. The results were judged based on the average mark among the 50 persons according to the following judgment criteria.

TABLE 5

| Mark | Usability | Adhesion | Finish | Makeup durability |
|---|---|---|---|---|
| 5 | Good | Good | Uniform | Good |
| 4 | Slightly good | Slightly good | Slightly uniform | Slightly good |
| 3 | Medium | Medium | Medium | Medium |
| 2 | Slightly bad | Slightly bad | Slightly non-uniform | Slightly bad |
| 1 | Bad | Bad | Non-uniform | Bad |

TABLE 6

(Judgment standard)

| Average value of marks | Judgment | |
|---|---|---|
| 4. 5 or more | Very good | ◎ |
| 3. not less than 4.5 and less than 5 | Good | ○ |
| 2. not less than 3.5 and less than 4.5 | Slightly bad | Δ |
| 1. less than 3.5 | Bad | X |

Example 12 and Comparative Example 12

Powder Foundations (Caked Powders)

TABLE 7

| | Ingredient composition | Mass % |
|---|---|---|
| 1 | Surface-treated powder in Example & Com. Exam. 2 | 35.0 |
| 2 | Nylon powder | 5.0 |
| 3 | Silica beads*1 | 6.0 |
| 4 | Surface-treated powder in Example 1 or Com. Exam. 1 | Balance |
| 5 | Surface-treated powder in Example 4 or Com. Exam. 4 | 7.0 |
| 6 | Surface-treated powder in Example 7 or Com. Exam. 7 | 1.6 |
| 7 | Surface-treated powder in Example 8 or Com. Exam. 8 | 0.5 |
| 8 | Surface-treated powder in Example 9 or Com. Exam. 9 | 0.1 |
| 9 | Methyl paraoxybenzoate | 0.2 |
| 10 | Neopentyl glycol 2-ethylhexanoate | 0.5 |
| 11 | Vaseline | 0.2 |

TABLE 7-continued

| | Ingredient composition | Mass % |
|---|---|---|
| 12 | Dimethylpolysiloxane*2 | 1.0 |
| 13 | Liquid paraffin | 1.0 |

*1God ball D11-796C (Suzuki Yushi Kogyo Co., Ltd.)
*2KF-96 (6cs) (Shin-Etsu Chemical Co., Ltd.)

(Producing Method)

A: Ingredients 1 to 9 were homogeneously mixed by a Henschel mixer.

B: Ingredients 10 to 13 were added to A, followed by further mixing.

C: B was pulverized by a pulverizer, which was compression molded with a gold
dish to obtain a powder foundation.

In the above table, Example 12 used Examples 1, 2, 4, 7, 8 and 9, and Comparative Example 12 used in Comparative Examples 1, 2, 4, 7, 8 and 9.

Results were shown in Table 8.

TABLE 8

| | Usability | Adhesion | Finish | Makeup durability |
|---|---|---|---|---|
| Example 12 | ◎ | ◎ | ◎ | ◎ |
| Com. Exam. 12 | ○ | Δ | Δ | Δ |

The powder foundation into which the cosmetic powders according to the present invention were blended was a cosmetic composition that had excellent usability and adhesion and excellent makeup durability. Further, they had less color dullness in the evaluation of the makeup durability as compared with Comparative Examples.

Example 13 and Comparative Example 13

Emulsified Foundations

TABLE 9

| | Ingredient composition | Mass % |
|---|---|---|
| 1 | Decamethylcyclopentasiloxane | 40.0 |
| 2 | Dimethylpolysiloxane*3 | 5.0 |
| 3 | Polyether-modified silicone*4 | 3.5 |
| 4 | Octadecyldimethylbenzyl ammonium salt-modified montmorillonite | 1.5 |
| 5 | Surface-treated powder in Example 3 & Com. Exam. 3 | 15.0 |
| 6 | Surface-treated powder in Example 4 & Com. Exam. 4 | 7.5 |
| 7 | Surface-treated powder in Example 7 & Com. Exam. 7 | 2.5 |
| 8 | Dipropylene glycol | 5.0 |
| 9 | Methyl paraoxybenzoate ester | 0.3 |
| 10 | Perfume | Appropriate amount |
| 11 | Purified water | Balance |

*3KF-96(6cs) (manufactured by Shin-Etsu Chemical Co., Ltd.)
*4KF-6017 (manufactured by Shin-Etsu Chemical Co., Ltd.)

(Producing Method)

A: Ingredients 1 to 4 were mixed under heating, Ingredients 5 to 7 were added thereto, and the resultant was made homogeneous.

B: Ingredients 8 to 9 and 11 were dissolved.

C: A was emulsified by gradually adding B thereto under stirring, and after cooling, a foundation was obtained by adding an ingredient 10 to the resultant.

In the above table, Example 13 used Examples 3, 4 and 7, whereas Comparative Example 13 used Comparative Examples 3, 4 and 7.

Results were shown in Table 10.

TABLE 10

|  | Usability | Adhesion | Finish | Makeup durability |
|---|---|---|---|---|
| Example 13 | ◎ | ◎ | ◎ | ◎ |
| Com. Exam. 13 | ○ | Δ | Δ | X |

The emulsified foundation into which the cosmetic powders according to the present invention were blended was a cosmetic composition that had excellent usability, adhesion, uniform finish and excellent makeup durability. In addition, they had less color dullness in the evaluation of the makeup durability as compared with Comparative Examples. The emulsified formulations according to the present invention also had excellent stability with lapse of time.

Example 14 and Comparative Example 14

Face Powders (Powdery)

TABLE 11

| Ingredient Composition | Mass % |
|---|---|
| 1 Surface-coated powder in Example 3 or Com. Exam. 3 | Balance |
| 2 Boron nitride | 15.0 |
| 3 Surface-coated powder in Example 6 or Com. Exam. 6 | 8.0 |
| 4 Bengala | 0.3 |
| 5 Black iron oxide | 0.2 |
| 6 Yellow iron oxide | 0.5 |
| 7 Surface-coated powder in Example 10 or Com. Exam. 10 | 8.0 |
| 8 Preservative (p-oxybenzoic acid ester) | Appropriate amount |
| 9 Perfume | Appropriate amount |

(Producing Method)
A: Ingredients 1 to 8 were homogeneously mixed by the Henschel mixer, and an ingredient 9 was added thereto, followed by further mixing.
B: A was pulverized by the pulverizer.
C: A powdery face powder was obtained by filling B into a vessel.

In the above table, Example 14 used Examples 3, 6 and 10, whereas Comparative Example 14 used Comparative Examples 3, 6 and 10.

Results were shown in Table 12.

TABLE 12

|  | Usability | Adhesion | Finish | Makeup durability |
|---|---|---|---|---|
| Example 14 | ◎ | ◎ | ◎ | ◎ |
| Com. Exam. 14 | ○ | X | Δ | ○ |

The face powder into which the cosmetic powders according to the present invention were blended was a cosmetic composition that had excellent usability and adhesion, uniform finish and makeup durability. In addition, it had less color dullness in the evaluation of the makeup durability as compared with Comparative Examples.

Example 15 and Comparative Example 15

Eye Shadows

TABLE 13

| Ingredient composition | Mass % |
|---|---|
| 1 Decamethylcyclopentasiloxane | 15.0 |
| 2 Dimethylpolysiloxane*5 | 10.0 |
| 3 Polyether-modified branched silicone*6 | 2.0 |
| 4 PEG(10) Lauryl ether | 0.5 |
| 5 Surface-treated powder in Example 6 or Com. Exam. 6 | 15.0 |
| 6 Surface-treated powder in Example 3 or Com. Exam. 3 | 8.0 |
| 7 Surface-treated powder in Example 4 or Com. Exam. 4 | 3.0 |
| 8 Stearoyl glutamic acid-treated inorganic colorant powder | Appropriate amount |
| 9 Sodium chloride | 2.0 |
| 10 Propylene glycol | 8.0 |
| 11 Preservative | Appropriate amount |
| 12 Perfume | Appropriate amount |
| 13 Purified water | Balance |

*5KF-96(6cs) (manufactured by Shin-Etsu Chemical Co., Ltd.)
*6Polyether-modified branched silicone; KF-6028 (manufactured by Shin-Etsu Chemical Co., Ltd.)

(Producing Method)
A: Ingredients 1 to 4 were mixed, and ingredients 5 to 8 were mixed thereto, followed by uniformly dispersing.
B: Ingredients 9 to 11 and 13 were uniformly dissolved.
C: B was gradually added to A under stirring, and an ingredient 12 was added thereto to obtain an eye shadow.

In the above table, Example 15 used Examples 3, 4 and 6, and Comparative Example 15 used Comparative Examples 3, 4 and 6.

Results were shown in Table 14.

TABLE 14

|  | Usability | Adhesion | Finish | Makeup durability |
|---|---|---|---|---|
| Example 15 | ◎ | ◎ | ◎ | ◎ |
| Com. Exam. 15 | Δ | X | Δ | Δ |

The eye shadow into which the cosmetic powders according to the present invention were blended was a cosmetic composition that had excellent usability and adhesion, uniform finish, and excellent makeup durability. In addition, it had less color dullness in the evaluation of the makeup durability as compared with Comparative Example.

Example 16 and Comparative Example 16

Mascaras

TABLE 15

| Ingredient composition | Mass % |
|---|---|
| 1 Paraffin wax | 5.0 |
| 2 Soft liquid isoparaffin | Balance |
| 3 Capryl mechicone | 0.5 |
| 4 Mixture of dimethicon/vinyl dimechicone cross-polymer and dimechicone*7 | 1.5 |
| 5 Trioctanoin | 13.0 |
| 6 Decamethylcyclopentasiloxane | 20.0 |
| 7 Stearoyl inulin | 5.0 |

TABLE 15-continued

| Ingredient composition | Mass % |
| --- | --- |
| 8 Dimethicon crosspolymer*8 | 10.0 |
| 9 Surface-treated powder in Example 9 or Com. Exam. 9 | 6.0 |
| 10 Sucrose fatty acid ester | 4.0 |
| 11 Bees wax | 5.0 |
| 12 Pentaerythrite rosinate | 5.0 |
| 13 Preservative | Appropriate amount |
| 14 Purified water | 5.0 |

*7KSG-16 (manufactured by Shin-Etsu Chemical Co., Ltd.)
*89040 Silicone Elastomer Blend (manufactured by Dow Corning Corp.)

(Producing Method)

Ingredients 1 to 12 were heated, mixed and dispersed, and then a mixture of ingredients 13 to 14 was mixed thereto, followed by emulsification and filling in a vessel.

In the above table, Example 16 used Example 9, and Comparative Example 16 used Comparative Example 9.

Results were shown in Table 16.

TABLE 16

| | Usability | Adhesion | Finish | Makeup durability |
| --- | --- | --- | --- | --- |
| Example 16 | ◎ | ◎ | ◎ | ◎ |
| Com. Exam. 16 | Δ | Δ | Δ | Δ |

The mascara into which the cosmetic powder according to the present invention was blended was a cosmetic composition that had excellent usability and adhesion, uniform finish and excellent makeup durability. In addition, it had less color dullness in the evaluation of the makeup durability as compared with Comparative Example.

Example 17 and Comparative Example 17

Foundation Creams

TABLE 17

| Ingredient composition | Mass % |
| --- | --- |
| 1 Dimethylpolysiloxane*9 | 2.0 |
| 2 Decamethylcyclopentasiloxane | 10.0 |
| 3 Polyether-modified silicone*10 | 3.0 |
| 4 Cetyl Isoctanate | 5.0 |
| 5 Vinyldimethicon/methiconsesquioxane cross-polymer*11 | 3.0 |
| 6 2-ethylhexyl paramethoxycinnamate | 2.0 |
| 7 Silicone elastomer *12 | 4.0 |
| 8 Organically modified bentonite | 0.5 |
| 9 Surface-treated powder in Example 3 or Com. Exam. 3 | 2.0 |
| 10 Surface-treated powder in Example 1 or Com. Exam. 1 | 1.0 |
| 11 Nylon powder | 3.0 |
| 12 Preservative | Appropriate amount |
| 13 Xanthan gum | 0.1 |
| 14 Magnesium L-ascorbate phosphate | 0.3 |
| 15 Purified water | Balance |

*9KF-96(2cs) (manufactured by Shin-Etsu Chemical Co., Ltd.)
*10SS-2910 (manufactured by Dow Corning Toray, Co., Ltd.)
*11KSP-100 (manufactured by Shin-Etsu Chemical Co., Ltd.)
*12 9045 Silicone Elastomer Blond (manufactured by Dow Corning Corp.)

(Producing Method)

Step 1: Ingredients 1 to 11 were mixed and dispersed.

Step 2: A mixture of ingredients 12 to 15 was added to the composition obtained in Step 1, followed by emulsification at room temperature.

In the above table, Example 17 used Examples 1 and 3, and Comparative Example 17 used Comparative Example 1 and 3.

Results were shown in Table 18.

TABLE 18

| | Usability | Adhesion | Finish | Makeup durability |
| --- | --- | --- | --- | --- |
| Example 17 | ◎ | ◎ | ◎ | ◎ |
| Com. Exam. 17 | Δ | Δ | Δ | X |

The foundation cream into which the cosmetic powders according to the present invention were blended was a cosmetic composition that had excellent usability and adhesion, uniform finish and makeup durability. The formulation according to the present invention also had excellent stability with lapse of time.

Example 18 and Comparative Example 18

Lipsticks

TABLE 19

| Ingredient composition | Mass % |
| --- | --- |
| 1 Candelilla wax | 8.0 |
| 2 Polyethylene wax | 8.0 |
| 3 Acrylsilicone resin containing long-chain alkyl*13 | 12.0 |
| 4 Methylphenylpolysiloxane*14 | 3.0 |
| 5 Isotridecyl isononanoate | 20.0 |
| 6 Glyceryl isostearate | 16.0 |
| 7 Polyglyceryl triisostearate | 28.5 |
| 8 Surface-treated powder in Example 6 or Com. Exam. 8 | 3.0 |
| 9 Surface-treated powder in Example 8 or Com. Exam. 8 | 0.6 |
| 10 Organic pigment | Appropriate amount |
| 11 Perfume | Appropriate amount |

*13KF-561P (manufactured by Shin-Etsu Chemical Co., Ltd.)
*14KF-54 (manufactured by Dow Corning Toray, Co., Ltd.)

(Producing Method)

A: Ingredients 1 to 6 and a part of an ingredient 7 were heated, mixed and dissolved.

B: Ingredients 8 to 10 and the remainder of the ingredient 7 were homogeneously mixed, which was added to A, followed by homogenization.

C: An ingredient 11 was added to B, thereby obtaining a lipstick.

In the above table, Example 18 used Examples 6 and 8, and Comparative Example 18 used Comparative Example 6 and 8.

Results were shown in Table 20.

TABLE 20

| | Usability | Adhesion | Finish | Makeup durability |
| --- | --- | --- | --- | --- |
| Example 18 | ◎ | ◎ | ◎ | ◎ |
| Com. Exam. 18 | Δ | Δ | Δ | Δ |

The lipstick into which the cosmetic powders according to the present invention were blended was a cosmetic composition that had excellent usability and adhesion, uniform finish, and excellent makeup durability. In addition, it had less color dullness in the evaluation of the makeup durability as compared with Comparative Example. The formulation according to the present invention had excellent stability with lapse of time.

Example 19 and Comparative Example 19

Eyeliners

TABLE 21

| Ingredient composition | Mass % |
|---|---|
| 1 Decamethylcyclopentasiloxane | 39.0 |
| 2 Polyether-modified silicone*15 | 3.0 |
| 3 Organic silicone resin*16 | 15.0 |
| 4 Dioctadecyldimethyl ammonium salt-modified montmorillonite | 3.0 |
| 5 Surface-treated powder in Example 9 or Com. Exam. 9 | 8.0 |
| 6 Surface-treated powder in Example 3 or Com. Exam. 3 | 2.0 |
| 7 1,3-Butylene glycol | 5.0 |
| 8 Sodium dehydroacetate | Appropriate amount |
| 9 Preservative | Appropriate amount |
| 10 Purified water | Balance |
| Total | 100 |

*15KF-6017 (manufactured by Shin-Etsu Chemical Co., Ltd.)
*16KF-7312J (manufactured by Shin-Etsu Chemical Co., Ltd.)

(Producing Method)
A: Ingredients 1 to 4 were mixed, ingredients 5 and 6 were added thereto, and the resultant was homogeneously mixed and dispersed.
B: Ingredients 7 to 10 were mixed.
C: B was gradually added to A, followed by emulsification to obtain an eye liner.

In the above table, Example 19 used Examples 3 and 9, and Comparative Example 19 used Comparative Example 3 and 9.

Results were shown in Table 22.

TABLE 22

| | Usability | Adhesion | Finish | Makeup durability |
|---|---|---|---|---|
| Example 19 | ⊚ | ⊚ | ⊚ | ⊚ |
| Com. Exam. 19 | Δ | X | X | Δ |

The eye liner into which the cosmetic powders according to the present invention were blended was a cosmetic composition that had excellent usability and adhesion, uniform finish and excellent makeup durability. In addition, it had less color dullness in the evaluation of the makeup durability as compared with Comparative Example. The emulsification formulation according to the present invention also had excellent stability with lapse of time.

Example 20 and Comparative Example 20

Liquid Emulsified Foundations

TABLE 23

| Ingredient composition | Mass % |
|---|---|
| 1 Dimethylpolysiloxane*17 | 4.5 |
| 2 Decamethylcyclopentasiloxane | 15.0 |

TABLE 23-continued

| Ingredient composition | Mass % |
|---|---|
| 3 Squalan | 4.0 |
| 4 Neopentyl glycol dioctanate | 3.0 |
| 5 Diglyceride myristate isostearate | 2.0 |
| 6 α-monoisostearyl glyceryl ether | 1.0 |
| 7 Polyether-modified silicone*18 | 1.0 |
| 8 Alkyl-Polyether co-modified silicone*19 | 0.5 |
| 9 Aluminum distearate | 0.2 |
| 10 Surface-treated powder in Example 1 or Com. Exam. 1 | 2.0 |
| 11 Surface-treated powder in Example 3 or Com. Exam. 3 | 5.0 |
| 12 Isostearyl sebacate-treated iron oxide powder | Appropriate amount |
| 13 Glycerin | 3.0 |
| 14 Preservative | Appropriate amount |
| 15 Perfume | Appropriate amount |
| 16 Purified water | Balance |

*17KF-96 (6cs) (manufactured by Shin-Etsu Chemical Co., Ltd.)
*18KF-6017 (manufactured by Shin-Etsu Chemical Co., Ltd.)
*19KF-6038 (manufactured by Shin-Etsu Chemical Co., Ltd.)

(Producing Method)
A: Ingredients 1 to 9 were heated and mixed, ingredients 10 to 12 were gradually added thereto, and the resultant was homogenized.
B: Ingredients 13 to 14 and 16 were heated and dissolved.
C: B was gradually added to A, followed by emulsifying and cooling, and an ingredient 15 was added thereto to obtain a liquid emulsified foundation.

In the above table, Example 20 used Examples 1 and 3, and Comparative Example 20 used Comparative Example 1 and 3.

Results were shown in Table 24.

TABLE 24

| | Usability | Adhesion | Finish | Makeup durability |
|---|---|---|---|---|
| Example 20 | ⊚ | ⊚ | ⊚ | ⊚ |
| Com. Exam. 20 | ○ | Δ | Δ | Δ |

The liquid foundation into which the cosmetic powders according to the present invention were blended was a cosmetic composition that had excellent usability and adhesion, uniform finish and excellent makeup durability. In addition, it had less color dullness in the evaluation of the makeup durability as compared with Comparative Example. The emulsification formulation according to the present invention also had excellent stability with lapse of time.

Example 21 and Comparative Example 21

Oily Caked Foundations

TABLE 25

| Ingredient composition | Mass % |
|---|---|
| 1 Polyethylene wax | 4.0 |
| 2 Paraffin | 4.0 |
| 3 Isononyl Isonanoate | 5.0 |
| 4 Dimethylpolysiloxane*20 | 10.0 |
| 5 Methylphenylpolysiloxane*21 | 10.0 |
| 6 Caprylic/Capric Triglyceride | 10.0 |
| 7 Surface-treated powder in Example 7 or Com. Exam. 7 | 3.5 |
| 8 Surface-treated powder in Example 8 or Com. Exam. 8 | 1.0 |
| 9 Surface-treated powder in Example 9 or Com. Exam. 9 | 0.3 |

TABLE 25-continued

| | Ingredient composition | Mass % |
|---|---|---|
| 10 | Surface-treated powder in Example 2 or Com. Exam. 2 | 20.0 |
| 11 | Surface-treated powder in Example 5 or Com. Exam. 5 | 15.0 |
| 12 | Surface-treated powder in Example 1 or Com. Exam. 1 | 5.2 |
| 13 | Polymethylsilsesquioxane*22 | 5.0 |
| 14 | Cellulose powder*23 | 5.0 |
| 15 | Silicone powder | 2.0 |

*20KF-96 (6cs) (manufactured by Shin-Etsu Chemical Co., Ltd.)
*21FZ-209 (manufactured by Dow Corning Toray Co., Ltd.)
*22Tospearl 145A (manufactured by c Co., Ltd..)
*23KC flock W-200 (manufactured by Nippon Paper Industries Co., Ltd.)
*24KSP-300 (manufactured by Nippon Paper Industries Co., Ltd.)

(Producing Method)

A: Ingredients 1 to 6 were heated and mixed.

B: Ingredients 7 to 15 were uniformly mixed, which was added to A, and the resultant was homogeneously kneaded.

Thereafter, the resultant was melted again and degassed, which was filled in a special container to obtain a product.

In the above table, Example 21 used Examples 1, 2, 5, 7, 8 and 9, and Comparative Example 21 used Comparative Examples 1, 2, 5, 7, 8 and 9.

Results were shown in Table 26.

TABLE 26

| | Usability | Adhesion | Finish | Makeup durability |
|---|---|---|---|---|
| Example 21 | ◎ | ◎ | ◎ | ◎ |
| Com. Exam. 21 | ○ | Δ | X | Δ |

The oily solid foundation into which the cosmetic powders according to the present invention were blended was a cosmetic composition that had excellent usability and adhesion, uniform finish, and makeup durability. In addition, it had less color dullness in the evaluation of the makeup durability as compared with Comparative Example.

Example 22 and Comparative Example 22

Stick-Like Concealers

TABLE 27

| | Ingredient composition | Mass % |
|---|---|---|
| 1 | Synthesized hydrocarbon wax | 4.0 |
| 2 | Paraffin | 3.0 |
| 3 | Ceresine | 2.0 |
| 4 | Polyethylene wax | 1.0 |
| 5 | α-Olefin oligomer*25 | 10.0 |
| 6 | Octyl polyhydroxystearate | 15.0 |
| 7 | Dipentaerythrite hexaoxystearate*26 | 5.0 |
| 8 | Dipentaerythrityl pentaisostearate | 5.0 |
| 9 | Isopropyl isostearate | 9.0 |
| 10 | Surface-treated powder in Exampls 7 or Com. Exam. 7 | 4.5 |
| 11 | Surface-treated powder in Example 8 or Com. Exam. 8 | 1.2 |
| 12 | Surface-treated powder in Example 9 or Com. Exam. 9 | 0.6 |
| 13 | Surface-treated powder in Example 2 or Com. Exam. 2 | 25.0 |
| 14 | Surface-treated powder in Example 4 or Com. Exam. 4 | 10.0 |
| 15 | Surface-treated powder in Example 10 or Com. Exam. 10 | 3.7 |
| 16 | Cellulose powder*27 | 1.0 |

*25Nomcoat HPD-C (manufactured by The Nisshin OilliO Group,Ltd.)
*26Cosmore (manufactured by The Nisshin OilliO Group,Ltd.)
*27KC Floc W-200 (manufactured by Nippon Paper Industries Co., Ltd.)

(Producing Method)

After oily ingredients were melted, powdery ingredients were mixed therewith, and the resultant was further mixed by using rollers. Then, the resultant was melted again, degassed, and filled in a mold. After cooling, the molded product was taken out, and placed in a container to obtain a product.

In the above table, Example 22 used Examples 1, 2, 4, 7, 8 and 9, and Comparative Example 22 used Comparative Examples 1, 2, 4, 7, 8 and 9.

Results were shown in Table 28.

TABLE 28

| | Usability | Adhesion | Finish | Makeup durability |
|---|---|---|---|---|
| Example 22 | ◎ | ◎ | ◎ | ◎ |
| Com. Exam. 22 | Δ | Δ | X | Δ |

The stick-like concealer into which the cosmetic powders according to the present invention were blended was a cosmetic composition that had excellent usability and adhesion, uniform finish, and excellent makeup duration.

Example 23 and Comparative Example 23

Water-in-Oil Creams

TABLE 29

| | Ingredient composition | Mass % |
|---|---|---|
| 1 | Dimethylpolysiloxane*28 | 6.0 |
| 2 | Methylphenylpolysiloxane*29 | 4.0 |
| 3 | Squalan | 5.0 |
| 4 | Neopentylglycol dioctanate | 3.0 |
| 5 | Polyether-modified silicone*30 | 3.0 |
| 6 | Surface-treated powder in Example 10 or Com. Exam. 10 | 1.0 |
| 7 | Surface-treated powder in Example or Com. Exam. 3 | 2.0 |
| 8 | Glycerin | 10.0 |
| 9 | Preservative | Appropriate amount |
| 10 | Perfume | Appropriate amount |
| 11 | Purified water | Balance |

*28KF-96 (6cs) (manufactured by Shin-Etsu Chemical Co., Ltd.)
*29KF-54 (manufactured by Shin-Etsu Chemical Co., Ltd.)
*30KF-6012 (manufactured by Shin-Etsu Chemical Co., Ltd.)

(Producing Method)

A: Ingredients 1 to 5 were mixed, ingredients 6 and 7 were mixed thereto, and the resultant was homogeneously mixed.

B: Ingredients 8 to 9 and 11 were mixed and melted.

C: After B was gradually added to A, followed by emulsification, an ingredient 10 was added thereto to obtain a cream.

In the above table, Example 23 used Examples 3 and 10, and Comparative Example 23 used Comparative Examples 3 and 10.

Results were shown in Table 30.

TABLE 30

| | Usability | Adhesion | Finish | Makeup durability |
|---|---|---|---|---|
| Example 23 | ◎ | ◎ | ◎ | ◎ |
| Com. Exam. 23 | Δ | X | Δ | ○ |

The water-in-oil cream into which the cosmetic powders according to the present invention were blended was a cosmetic composition that had excellent usability and adhesion, uniform finish, and excellent makeup durability. Further, the cream also had excellent stability with lapse of time.

Example 24 and Comparative Example 24

Oil-in-Water Type Creams

TABLE 31

| | Ingredient composition | Mass % |
|---|---|---|
| 1 | Mixture of dimethicon/vinyldimethicon crosspolymer and dimethicone*31 | 9.0 |
| 2 | glyceryl trioctanate | 5.0 |
| 3 | Surface-treated powder in Example 10 or Com. Exam. 10 | 2.0 |
| 4 | Dipropylene glycol | 7.0 |
| 5 | Glycerin | 5.0 |
| 6 | Methyl cellulose (2% aqueous solution)*32 | 7.0 |
| 7 | Polyacrylamide-based emulsifier*33 | 2.0 |
| 8 | Preservative | Appropriate amount |
| 9 | Perfume | Appropriate amount |
| 10 | Purified water | 63.0 |

*31 KSG-16 (manufactured Shin-Etsu Chemical Co., Ltd.)
*32 Metolose (manufactured by Shin-Etsu Chemical Co., Ltd.)
*33 Sepigel 305 (manufactured by SEPPIC Co., Ltd.)

(Producing Method)

A: Ingredients 4 to 10 were mixed.
B: Ingredients 1 to 3 were mixed, the mixture was added to A, and the resultant was stirred and emulsified.

In the above Table, Example 24 used Example 10, whereas Comparative Example 24 used Comparative Example 10.

Results were shown in Table 32.

TABLE 32

| | Usability | Adhesion | Finish | Makeup durability |
|---|---|---|---|---|
| Example 24 | ◎ | ◎ | ◎ | ◎ |
| Com. Exam. 24 | Δ | Δ | Δ | X |

The water-in-oil cream into which the cosmetic powder according to the present invention was blended was a cosmetic composition that had excellent usability and adhesion, uniform finish and makeup durability, Further, the cream also had excellent stability with lapse of time.

Example 25 and Comparative Example 25

Sunscreen Emulsions

TABLE 33

| | Ingredient composition | Mass % |
|---|---|---|
| 1 | Decamethylcyclopentasiloxane | 21.0 |
| 2 | Methylphenylpolysiloxane*34 | 3.0 |
| 3 | Sorbitan monoisostearate | 1.0 |
| 4 | Polyether-modified silicone*35 | 0.5 |
| 5 | Trimethylsiloxysilicate*36 | 1.0 |
| 6 | Octyl paramethoxycinnamate | 4.0 |

TABLE 33-continued

| | Ingredient composition | Mass % |
|---|---|---|
| 7 | Surface-treated powder in Example 6 or Com. Exam. 6 | 2.0 |
| 8 | Surface-treated powder in Example 11 or Com. Exam. 11 | 10.0 |
| 9 | Sorbitol | 2.0 |
| 10 | Sodium chloride | 2.0 |
| 11 | Preservative | Appropriate amount |
| 12 | Perfume | Appropriate amount |
| 13 | Purified water | Balance |

*34 KF-56 (manufactured by Shin-Etsu Chemical Co., Ltd.)
*35 KKF6015 (manufactured by Shin-Etsu Chemical Co., Ltd.)
*36 X-21-5250 (manufactured by Shin-Etsu Chemical Co., Ltd.)

(Producing Method)

A: Ingredients 1 to 6 were mixed, and ingredients 7 and 8 were uniformly dispersed therein.
B: Ingredients 9 to 11 and 13 were heated and mixed.
C: Under stirring, B was gradually added to A for emulsification, and an ingredient 12 was added thereto after cooling, thereby obtaining a sunscreen emulsion.

In the above table, Example 25 used Examples 6 and 11, and Comparative Example 25 used Comparative Examples 6 and 11.

Results were shown in Table 34.

TABLE 34

| | Usability | Adhesion | Finish | Makeup durability |
|---|---|---|---|---|
| Example 25 | ◎ | ◎ | ◎ | ◎ |
| Com. Exam. 25 | X | Δ | X | Δ |

The sunscreen emulsion into which the cosmetic powders according to the present invention were blended was a cosmetic composition that had excellent usability and adhesion with uniform finish and excellent makeup durability. Further, it also had excellent stability with lapse of time.

Example 26 and Comparative Example 26

UV Cut Creams

TABLE 35

| | Ingredient composition | Mass % |
|---|---|---|
| 1 | Decamethylcyclopentasiloxane | 17.0 |
| 2 | Acrylsilicone resin*37 | 12.0 |
| 3 | Glyceryl trioctanate | 5.0 |
| 4 | Octyl paramethoxy cinnamate | 6.0 |
| 5 | Mixture of crosslinked polyether-modified silicone and silicone oil*38 | 5.0 |
| 6 | Alkyl-silicone/polyether co-modified silicone*39 | 2.5 |
| 7 | Surface-treated powder in Example 10 or Com. Exam. 10 | 5.0 |
| 8 | Surface-treated powder in Example 11 or Com. Exam. 11 | 13.0 |
| 9 | Sodium chloride | 0.6 |
| 10 | 1,3-butylene glycol | 2.0 |
| 11 | Preservative | Appropriate amount |

TABLE 35-continued

| | Ingredient composition | Mass % |
|---|---|---|
| 12 | Perfume | Appropriate amount |
| 13 | Purified water | Balance |

*37Acryl silicone resin: KP-545 (manufactured by Shin-Etsu Chemical Co., Ltd.)
*38KSG-210 (manufactured by Shin-Etsu Chemical Co., Ltd.)
*39KF-6038 (manufactured by Shin-Etsu Chemical Co., Ltd.)

(Producing Method)

A: An ingredient 2 was added to a part of 1, the mixture was homogenized, and an ingredient 8 was added and dispersed thereinto by a bead mill.

B: The remainder of the ingredient 1 and ingredients 3 to 7 were mixed and homogenized.

C: Ingredients 9 to 11 and 13 were mixed and dissolved.

D: C was added to B, the mixture was emulsified, and A was dispersed therein, and an ingredient 12 was added thereinto, thereby obtaining a UV cut cream.

In the above table, Example 26 used Examples 10 and 11, and Comparative Example 26 used Comparative Examples 10 and 11.

Results were shown in Table 36.

TABLE 36

| | Usability | Adhesion | Finish | Makeup durability |
|---|---|---|---|---|
| Example 26 | ◎ | ◎ | ◎ | ◎ |
| Com. Exam. 26 | X | Δ | Δ | ◯ |

The UV cut cream into which the cosmetic powders according to the present invention were blended was a cosmetic composition that had excellent usability and adhesion with uniform finish and excellent makeup durability. Further, it also had excellent stability with lapse of time.

Examiner 27 and Comparative Example 27

Nail Enamels

TABLE 37

| | Ingredient composition | Mass % |
|---|---|---|
| 1 | Acrylsilicone resin*40 | 44.5 |
| 2 | Methyltrimechicone*41 | 5.0 |
| 3 | Nitrocellulose | 3.0 |
| 4 | Camphor | 0.5 |
| 5 | Acetyltributyl citrate | 1.0 |
| 6 | Dimethyldistearylammonium hectorite | 0.5 |
| 7 | Butyl acetate | 80.0 |
| 8 | Ethyl acetate | 10.0 |
| 9 | Isopropyl alcohol | 5.0 |
| 10 | Surface-treated powder in Example 6 or Com. Exam. 6 | 1.5 |

*40KF-549 (manufactured by Shin-Etsu Chemical Co., Ltd.)
*41TMF-1.5 (manufactured by Shin-Etsu Chemical Co., Ltd.)

(Producing Method)

A: Ingredients 7 to 9 were mixed, to which ingredients 4 to 6 were added and homogeneously mixed.

B: Ingredients 1 to 3 were added and mixed into A.

C: A nail enamel was obtained by adding and mixing an ingredient 10 into B.

In the above table, Example 27 used Example 6, and Comparative Example 27 used Comparative Example 6.

Results were shown in Table 38.

TABLE 38

| | Usability | Adhesion | Finish | Makeup durability |
|---|---|---|---|---|
| Example 27 | ◎ | ◎ | ◎ | ◎ |
| Com. Exam. 27 | Δ | Δ | Δ | ◯ |

The nail enamel into which the cosmetic powder according to the present invention was blended was a cosmetic composition that had excellent usability and adhesion with uniform finish and excellent makeup durability.

Example 28 and Comparative Example 28

Moisturizing Creams

TABLE 39

| | Ingredient composition | Mass % |
|---|---|---|
| 1 | Mixture of dimethicon/vinyldimethicone crosspolymer and dimechicone*42 | 5.0 |
| 2 | Decamethylcyclopentasiloxane | 5.0 |
| 3 | Phenyl trimechicone*43 | 3.0 |
| 4 | Liquid paraffin | 5.0 |
| 5 | Pentaerythritol tetra-2-ethylhexanoate | 3.0 |
| 6 | Cetyl 2-ethylhexanoate | 5.0 |
| 7 | Polyether-modified silicone*44 | 1.0 |
| 8 | Silicone elastomer powder*45 | 2.5 |
| 9 | Surface-treated powder in Example 10 or Com. Exam. 10 | 2.0 |
| 10 | Zinc stearate | 2.0 |
| 11 | Vitamin E acetate | 3.0 |
| 12 | Polyethylene glycol 400 | 1.0 |
| 13 | Sodium butyrate | 1.0 |
| 14 | 1,3-butylene glycol | 5.0 |
| 15 | Preservative | Appropriate amount |
| 16 | Perfume | Appropriate amount |
| 17 | Purified water | Balance |

*42KSG-16 (manufactured by Shin-Etsu Chemical Co., Ltd.)
*43SH556 (manufactured by Dow Corning Toray Co., Ltd.)
*44SS-2910 (manufactured by Dow Corning Toray Co., Ltd.)
*45Torefil E-506S (manufactured by Dow Corning Toray Co., Ltd.)

(Producing Procedure)

Step 1: Ingredients 1 to 7 and Ingredients 10 to 11 were homogeneously mixed, ingredients 8 to 9 were added thereto, and the resultant was homogeneously distributed.

Step 2: Ingredients 12 to 15 and ingredient 17 were added and dissolved.

Step 3: The composition obtained in Step 2 was gradually added to the composition obtained in Step 1, which was emulsified and cooled.

Step 4: An ingredient 16 was added to the composition obtained in Step 3, which was stirred and mixed.

In the above table, Example 28 used Example 10, and Comparative Example 28 used Comparative Example 10.

Results were shown in Table 40.

TABLE 40

|  | Usability | Adhesion | Finish | Makeup durability |
|---|---|---|---|---|
| Example 28 | ⊚ | ⊚ | ⊚ | ⊚ |
| Com. Exam. 28 | Δ | Δ | Δ | Δ |

The moist cream into which the cosmetic powder according to the present invention was blended was a cosmetic composition that had excellent usability and adhesion with uniform finish and excellent makeup durability.

Example 29 and Comparative Example 29

Aftershave Creams

TABLE 41

| | Ingredient composition | Mass % |
|---|---|---|
| 1 | Surface-treated powder in Example 10 or Com. Exam. 10 | 15.0 |
| 2 | Decamethylcyclopentasiloxane | 20.0 |
| 3 | Polyether-modified silicone*46 | 3.0 |
| 4 | Polyether-modified silicone*47 | 6.0 |
| 5 | Polyethylene glycol 400 | 5.0 |
| 6 | Sodium L-glutaminate | 2.0 |
| 7 | allantoin | 0.1 |
| 8 | Aloe extract | Appropriate amount |
| 9 | Preservative | Appropriate amount |
| 10 | Antioxidant | Appropriate amount |
| 11 | Perfume | Appropriate amount |
| 12 | Purified water | Balance |

*46SS-2910 (manufactured by Dow Corning Toray Co., Ltd.)
*475200 Formulation Aid (manufactured by Dow Corning Co., Ltd.)

(Producing Method)

A: Ingredients 1 to 5 and Ingredients 11 to 12 were heated and mixed.

B: Ingredients 6 to 10 were heated and mixed.

C: The composition obtained in Step 2 was gradually added to the composition obtained in Step 1.

In the above table, Example 29 used Example 10, and Comparative Example 29 used Comparative Example 10.

Results were shown in Table 42.

TABLE 42

|  | Usability |
|---|---|
| Example 29 | ⊚ |
| Com. Exam. 20 | Δ |

The aftershave cream into which the cosmetic powder according to the present invention was blended was a cosmetic composition that had excellent usability.

Example 30 and Comparative Example 30

Lip Gross

TABLE 43

| | Ingredient composition | Mass % |
|---|---|---|
| 1 | Polyamide-modified silicone*48 | 19.0 |
| 2 | Mixture of dimethicon/vinyldimethicone crosspolymer and dimechicone*49 | 7.0 |
| 3 | Methylphenylpolysiloxane | 28.0 |
| 4 | Isononyl isononanoate | 38.0 |
| 5 | Triethylhexanoin | 2.0 |
| 6 | Surface-treated powder in Example 6 or Com. Exam. 6 | 3.0 |

*482-8178 gellant (manufactured by Dow Corning Co., Ltd.)
*49KSG-18 (manufactured by Shin-Etsu Chemical Co., Ltd.)

(Producing Method)

Ingredients 1 to 6 were heated and mixed, filled in a vessel, and thereafter cooled.

In the above table, Example 30 used Example 6, and Comparative Example 30 used Comparative Example 6.

Results were shown in Table 44.

TABLE 44

|  | Usability | Adhesion | Finish | Makeup durability |
|---|---|---|---|---|
| Example 30 | ⊚ | ⊚ | ⊚ | ⊚ |
| Com. Exam. 30 | Δ | X | Δ | Δ |

The lip gross into which the cosmetic powder according to the present invention was blended was a cosmetic composition that had excellent usability and adhesion with uniform finish and excellent makeup durability.

Example 31 and Comparative Example 31

Shampoos

TABLE 45

| | Ingredient composition | Mass % |
|---|---|---|
| 1 | Purified water | Balance |
| 2 | Polyquaternium-10 | 0.3 |
| 3 | EDTA-2Na | 0.1 |
| 4 | Glycerin | 1.5 |
| 5 | Sodium laureth sulfate (27% aqueous solution) | 30.0 |
| 6 | Laureth-6 Na carboxylate (24% aqueous solution) | 10.0 |
| 7 | Cocamidopropyl betaine, NaCl (30% aqueous solution) | 10.0 |
| 8 | Surface-treated powder in Example 10 or Com. Exam. 10 | 0.5 |
| 9 | Preservative | Appropriate amount |
| 10 | Perfume | Appropriate amount |
| 11 | Cocamido MEA | 2.0 |
| 12 | Polyquaternium-7 | 0.27 |
| 13 | Citric acid | Appropriate amount |

(Producing Method)

A: Ingredients 1 to 4 are heated, mixed and dissolved.

B: Ingredients 5 to 8 are added to the composition obtained in Step 1.

C: The composition obtained in Step 2 is cooled, and ingredients 9 to 12 were added thereinto. If necessary, an ingredient 13 is added thereinto, and the pH of the resultant is adjusted.

In the above Table, Example 31 used Example 10, and Comparative Example 31 used Comparative Example 10.

Results were shown in Table 46.

TABLE 46

|  | Usability |
|---|---|
| Example 31 | ⊚ |
| Com. Exam. 31 | Δ |

The shampoo into which the cosmetic powder according to the present invention was blended had excellent usability.

Example 32 and Comparative Example 32

Conditioners

TABLE 47

| | Ingredient composition | Mass % |
|---|---|---|
| 1 | Stearyltomonium chloride | 1.44 |
| 2 | Cetyl alcohol | 2.4 |
| 3 | Octyl dodecanol | 0.5 |
| 4 | Cetyl ethylhexanoate | 0.6 |
| 5 | Squalan | 0.2 |
| 6 | Surface-treated powder in Example 10 or Com. Exam. 10 | 0.5 |
| 7 | Purified water | Balance |
| 8 | Glycerin | 2.0 |
| 9 | Preservative | Appropriate amount |
| 10 | Perfume | Appropriate amount |
| 13 | Citric acid | Appropriate amount |

(Producing Method)

A: Ingredients 1 to 6 are heated, mixed and melted.
B: Ingredients 7 to 8 are heated, mixed and dissolved.
C: The composition obtained in Step 1 is added to the composition obtained in Step 2, which is emulsified.
D: The composition obtained in Step 3 is cooled, and ingredients 9 and 10 are added thereto. If necessary, an ingredient 11 is added thereinto.

In the above Table, Example 32 used Example 10, and Comparative Example 32 used Comparative Example 10.

Results were shown in Table 48.

TABLE 48

|  | Usability |
|---|---|
| Example 32 | ⊚ |
| Com. Exam. 32 | Δ |

The conditioner into which the cosmetic powder according to the present invention was blended had excellent usability.

What is claimed is:

1. A method for producing a cosmetic powder surface-treated with a silicone gel, said method comprising:
treating surfaces of particles of a powder having an average particle diameter in the range of from 0.01 to 500 μm as a starting material with the silicone gel by forming the silicone gel thereon in an in-situ method that comprises hydrolyzing and condensing an organopolysiloxane containing at least (i) a diorganopolysiloxane with reactive opposite ends expressed by the following formula (1) and (ii) at least one crosslinking agent selected from the group consisting of (a) a silane coupling agent having the following formula (2) and at least two hydrolyzable groups per one molecule and (b) a reactive organopolysiloxane of the following formula (3):

(Chemical formula 1)

$$R^1R^2{}_2SiO-(R^2{}_2SiO)_L-SiR^1R^2{}_2 \quad (1)$$

wherein $R^1$ is a hydrolyzable group selected from the group consisting of a hydroxyl group, an amino group, an acetoxy group, an alkoxy group or a hydrogen atom, $R^2$ is a non-substituted or substituted $C_1$-$C_{20}$ monovalent hydrocarbon group, and L is 3 to 10,000;

(Chemical formula 2)

$$R^3R^4{}_nSiX_{(3-n)} \quad (2)$$

wherein $R^3$ is selected from the group consisting of a $C_1$-$C_{20}$ monovalent hydrocarbon group, an amino group, an aminoethyl group, a mercapto group, an isocyanate and a phenyl group, $R^4$ is selected from the group consisting of a phenyl group, a hydrogen atom, and a $C_1$-$C_3$ monovalent lower alkyl group, X is a hydroxyl group or an alkoxy group, and n is 0 or 1;

(Chemical formula 3)

$$R^5{}_3SiO-(R^5{}_2SiO)_n-SiR^5{}_3 \quad (3)$$

wherein $R^5$ is a hydrolyzable group or a non-substituted or substituted $C_1$-$C_{20}$ monovalent hydrocarbon group, the hydrolyzable group is a hydroxyl group, an amino group, an acetoxy group, an alkoxyl group or a hydrogen atom, n is 3 to 1,000, and at least three hydrolyzable groups are provided in one molecule;
a ratio between the diorganopolysiloxane with the reactive opposite ends and the crosslinking agent is in a compounding range of 100/0.1 to 100/35 wt %; and,
thermally fixing the surface-treated cosmetic powder and pulverizing a resultant,
wherein the silicone gel formed on the surfaces of the particles of the cosmetic powder has a finely three-dimensional crosslinking structure of the diorganopolysiloxane, and
when the silicone gel is obtained by effecting the method in the absence of the powder, the obtained silicone gel has a complex modulus of 3,000 to 100,000 Pa and a loss coefficient tan δ is 1.0 to 2.5 in measurement of a dynamic viscoelasticity under a distortion factor of 17% at 25° C. and a shear frequency of 4 Hz, and a measured value of the silicone gel measured by a measuring method with a durometer AO is 0.

2. The method for producing the cosmetic powder surface-treated with the silicone gel set forth in claim 1, wherein the diorganopolysiloxane with the reactive opposite ends is used in the form of a water emulsion.

3. The method for producing the cosmetic powder surface-treated with the silicone gel set forth in claim 1, wherein the cosmetic powder surface-treated with the silicone gel is obtained through hydrolyzing/condensing at least a part of (i) the diorganopolysiloxane having the opposite reactive ends of the formula (1) and (ii) the at least one crosslinking agent selected from the group consisting of (a) the silane coupling agent having the following formula (2) and at least two hydrolyzable groups per one molecule and (b) the reactive organopolysiloxane of the following formula (3) in a step:

(A) of mixing a water-soluble solvent and the cosmetic powder as the starting material, and separately or simultaneously adding (i) the diorganopolysiloxane with the reactive opposite ends expressed by the formula (1) and (ii) the at least one crosslinking agent selected from the group consisting of (a) the silane coupling agent having the formula (2) and at least two hydrolyzable groups per one molecule and (b) the reactive organopolysiloxane of the formula (3) under the presence of the cosmetic powder as the starting material in a state that the water-soluble solvent and the cosmetic powder are mixed and the mixed state of the water-soluble solvent and the cosmetic powder is either a capillary or slurry, or (B) of adding the crosslinking agent selected from the group consisting of (a) the silane coupling agent having the formula (2) and at least two hydrolyzable groups per one molecule and (b) the reactive organopolysiloxane of the formula (3) under the presence of the cosmetic powder as the starting material in the state that the water-soluble solvent, the cosmetic powder, and the diorganopolysiloxane of the formula (1) are mixed and the mixed state thereof is a capillary, followed by thermally fixing and pulverizing.

4. The method for producing the cosmetic powder surface-treated with the silicone gel set forth in claim 1, wherein the cosmetic powder is an inorganic powder, an organic powder or a composite powder thereof.

5. The method for producing the cosmetic powder surface-treated with the silicone gel set forth in claim 1, wherein the silicone gel is obtained by hydrolyzing/condensing the diorganopolysiloxane having the opposite reactive ends of the formula (1) and the silane coupling agent of the formula (2) having at least two hydrolysable groups per one molecule.

6. The method for producing the cosmetic powder surface-treated with the silicone gel set forth in claim 1, wherein the diorganopolysiloxane of the formula (1) is dimethiconol.

7. The method for producing the cosmetic powder surface-treated with the silicone gel set forth in claim 6, wherein a water emulsion obtained by mechanically emulsifying the dimethiconol having a number L of dimethylsiloxane unit of the formula (1) being 3 to 1,000 is used as the starting material for the surface treatment.

8. The method for producing the cosmetic powder surface-treated with the silicone gel set forth in claim 6, wherein a water emulsion obtained by emulsion polymerizing the dimethiconol having the number L of the dimethylsiloxane units of the formula (1) being 3 to 1,000 is used as the starting material for the surface treatment.

9. The method for producing the cosmetic powder surface-treated with the silicone gel set forth in claim 6, wherein a water emulsion of the dimethiconol obtained by emulsion polymerizing with a starting material of octamethylcyclotetrasiloxane is used as the starting material for the surface treatment.

10. The method for producing the cosmetic powder surface-treated with the silicone gel set forth in claim 6, wherein a surface active agent is contained in the water emulsion of the dimethiconol, and the surface active agent contains at least an acylated amino acid.

11. The method for producing the cosmetic powder surface-treated with the silicone gel set forth in claim 7, wherein a mixing weight ratio (B)/(A)×100 between the weight of the dimethiconol (A) and the weight of a surface-active agent (B) in the water emulsion of the dimethiconol is less than 6.0.

12. The method for producing the cosmetic powder surface-treated with the silicone gel set forth in claim 1, wherein the organic group $R^3$ of a silane coupling agent in the formula (2) is either the amino group or the phenyl group.

13. The method for producing the cosmetic powder surface-treated with the silicone gel set forth in claim 1, wherein the weight ratio between the silicone gel and the cosmetic powder is 100/0.1 to 100/25.0 in weight ratio.

14. A cosmetic powder surface-treated with a silicone gel, said powder having particles with an average particle diameter in a range of from 0.01 to 500 μm as a starting material that are surface-treated with a silicone gel by forming the silicone gel thereon in an in-situ method that comprises hydrolyzing and condensing an organopolysiloxane containing at least (i) a diorganopolysiloxane with reactive opposite ends expressed by the following formula (1) and (ii) at least one crosslinking agent selected from the group consisting of (a) a silane coupling agent having the following formula (2) and at least two hydrolyzable groups per one molecule and (b) a reactive organopolysiloxane of the following formula (3) as a crosslinking agent:

(Chemical formula 1)

$$R^1R^2{}_2SiO\text{---}(R^2{}_2SiO)_L\text{---}SiR^1R^2{}_2 \qquad (1)$$

wherein $R^1$ is a hydrolyzable group selected from the group consisting of a hydroxyl group, an amino group, an acetoxy group, an alkoxy group or a hydrogen atom, $R^2$ is a non-substituted or substituted $C_1$-$C_{20}$ monovalent hydrocarbon group, and L is 3 to 10,000;

(Chemical formula 2)

$$R^3R^4{}_nSiX_{(3-n)} \qquad (2)$$

wherein $R^3$ is selected from the group consisting of a $C_1$-$C_{20}$ monovalent hydrocarbon group, an amino group, an aminoethyl group, a mercapto group, an isocyanate and a phenyl group, $R^4$ is selected from the group consisting of a phenyl group, a hydrogen atom, and a $C_1$-$C_3$ monovalent lower alkyl group, X is a hydroxyl group or an alkoxy group, and n is 0 or 1;

(Chemical formula 3)

$$R^5{}_3SiO\text{---}(R^5{}_2SiO)_n\text{---}SiR^5{}_3 \qquad (3)$$

wherein $R^5$ is a hydrolyzable group or a non-substituted or substituted $C_1$-$C_{20}$ monovalent hydrocarbon group, the hydrolyzable group is a hydroxyl group, an amino group, an acetoxy group, an alkoxyl group or a hydrogen atom, n is 3 to 1,000, and at least three hydrolyzable groups are provided in one molecule, a ratio between the diorganopolysiloxane with the reactive opposite ends and the crosslinking agent is in a compounding range of 100/0.1 to 100/35 wt %, and the silicone gel has a finely three-dimensional crosslinking structure of the diorganopolysiloxane, and when the silicone gel is obtained by effecting the method in the absence of the powder, the silicone gel has a complex modulus of 3,000 to 100,000 Pa and a loss coefficient tan δ is 1.0 to 2.5 in measurement of a dynamic viscoelasticity under a distortion factor of 17% at 25° C. and a shear frequency of 4 Hz, and a measured value of the silicone gel measured by a measuring method with a durometer AO is 0.

15. The cosmetic powder surface-treated with a silicone gel set forth in claim 14, wherein the silicone gel is deposited onto surfaces of particles of a powder as a starting material in an in-situ method and then thermally fixed in the presence of the powder by hydrolyzing/condensing at least a part of a mixture of (i) the diorganopolysiloxane with the reactive opposite ends of the formula (1) and (ii) the at least one crosslinking agent selected from the group consisting of (a) the silane coupling agent having the formula (2) and at least two hydrolyzable groups per one molecule and (b) the reactive organopolysiloxane of the formula (3).

16. The cosmetic powder surface-treated with the silicone gel set forth in claim 14, wherein the diorganopolysiloxane with the reactive opposite ends is used in the form of a water emulsion.

17. The cosmetic powder surface-treated with the silicone gel set forth in claim 14, wherein the cosmetic powder surface-treated with the silicone gel is obtained through hydrolyzing/condensing at least a part of (i) the diorganopolysiloxane having the opposite reactive ends of the formula (1) and (ii) the at least one crosslinking agent selected from the group consisting of (a) the silane coupling agent having the formula (2) and at least two hydrolyzable groups per one molecule and (b) the reactive organopolysiloxane of the formula (3) in a step:
  (A) by mixing a water-soluble solvent and the cosmetic powder as the starting material, and separately or simultaneously adding (i) the diorganopolysiloxane with the reactive opposite ends expressed by the formula (1) and (ii) the at least one crosslinking agent selected from the group consisting of (a) the silane coupling agent having the formula (2) and at least two hydrolyzable groups per one molecule and (b) the reactive organopolysiloxane of the formula (3) in a state that the water-soluble solvent and the cosmetic powder are mixed and the mixed state of the water-soluble solvent and the cosmetic powder is either a capillary or slurry followed by fixing under heating, or
  (B) by adding the crosslinking agent composed of at least one kind of the silane coupling agent of the formula (2) and the reactive organopolysiloxane of the formula (3) in the presence of the cosmetic powder as the starting material in the state that the water-soluble solvent, the cosmetic powder, and the diorganopolysiloxane of the formula (1) are mixed and the mixed state thereof is a capillary, followed by fixing under heating and pulverizing.

18. The cosmetic powder surface-treated with the silicone gel set forth claim 14, wherein the cosmetic powder is an inorganic powder, an organic powder or a composite powder thereof.

19. The cosmetic powder surface-treated with the silicone gel set forth in claim 14, wherein the silicone gel is obtained by hydrolyzing/condensing the diorganopolysiloxane having the opposite reactive ends of the formula (1) and the silane coupling agent of the formula (2) having at least two hydrolyzable groups per one molecule.

20. The cosmetic powder surface-treated with a silicone gel set forth in claim 14, wherein the diorganopolysiloxane of the formula (1) is dimethiconol.

21. The cosmetic powder surface-treated with a silicone gel set forth in claim 20, wherein a water emulsion obtained by mechanically emulsifying the dimethiconol having a number L of dimethylsiloxane unit of the formula (1) being 3 to 1,000 is used as a starting material for the surface treatment.

22. The cosmetic powder surface-treated with a silicone gel set forth in claim 20, wherein the water emulsion obtained by emulsion polymerizing the dimethiconol having the number L of the dimethylsiloxane units of the formula (1) being 3 to 1,000 is used as the starting material for the surface treatment.

23. The cosmetic powder surface-treated with a silicone gel set forth in claim 20, wherein the water emulsion of the dimethiconol obtained by emulsion polymerizing with a starting material of octamethylcyclotetrasiloxane is used as the starting material for the surface treatment.

24. The cosmetic powder surface-treated with a silicone gel set forth in claim 20, wherein a surface active agent is contained in the water emulsion of the dimethiconol, and the surface active agent contains at least an acylated amino acid.

25. The cosmetic powder surface-treated with a silicone gel set forth in any of claim 21, wherein a mixing weight ratio (B)/(A)×100 between the weight of the dimethiconol (A) and the weight of a surface-active agent (B) in the water emulsion of the dimethiconol is less than 6.0.

26. The cosmetic powder surface-treated with a silicone gel set forth in claim 14, wherein the organic group $R^3$ of a silane coupling agent in the formula (2) is either the amino group or the phenyl group.

27. The cosmetic powder surface-treated with a silicone gel set forth in claim 14, wherein the weight ratio between the silicone gel and the cosmetic powder is 100/0.1 to 100/25.0.

28. A method for producing a cosmetic composition containing at least 0.1 wt % of a cosmetic powder surface-treated with a silicone gel, comprising the steps of:
  preparing said cosmetic powder surface-treated with the silicone gel as set forth in claim 1; and
  mixing said cosmetic powder surface-treated with the silicone gel with a cosmetic composition.

29. A cosmetic composition containing at least 0.1 wt % of the cosmetic powder surface-treated with the silicone gel produced by the method as set forth in claim 1.

* * * * *